US012807617B2

(12) United States Patent
Li et al.

(10) Patent No.: US 12,807,617 B2
(45) Date of Patent: Nov. 24, 2026

(54) FUSED TRICYCLIC CYCLIN-DEPENDENT KINASE INHIBITOR, AND PREPARATION METHOD THEREFOR AND PHARMACEUTICAL USE THEREOF

(71) Applicant: Jiangsu Hengrui Pharmaceuticals Co., Ltd., Jiangsu (CN)

(72) Inventors: Yunfei Li, Shanghai (CN); Haomiao Liu, Shanghai (CN); Hao Zou, Shanghai (CN); Zhen Zhang, Shanghai (CN); Xiaming Pang, Shanghai (CN); Honglong Gong, Shanghai (CN); Chao Zhang, Shanghai (CN); Fang Zhang, Shanghai (CN)

(73) Assignee: Jiangsu Hengrui Pharmaceuticals Co., Ltd., Jiangsu (CN)

( * ) Notice: Subject to any disclaimer, the term of this patent is extended or adjusted under 35 U.S.C. 154(b) by 543 days.

(21) Appl. No.: 18/263,870

(22) PCT Filed: Jan. 28, 2022

(86) PCT No.: PCT/CN2022/074509

§ 371 (c)(1),
(2) Date: Aug. 1, 2023

(87) PCT Pub. No.: WO2022/166799

PCT Pub. Date: Aug. 11, 2022

(65) Prior Publication Data

US 2024/0140963 A1 May 2, 2024

(30) Foreign Application Priority Data

Feb. 3, 2021 (CN) ......................... 202110152320.9
Mar. 30, 2021 (CN) ......................... 202110342800.1
Apr. 30, 2021 (CN) ......................... 202110485700.4
Jun. 16, 2021 (CN) ......................... 202110667137.2

(51) Int. Cl.
*C07D 498/06* (2006.01)
*C07B 59/00* (2006.01)
*C07D 471/06* (2006.01)

(52) U.S. Cl.
CPC .......... *C07D 498/06* (2013.01); *C07B 59/002* (2013.01); *C07D 471/06* (2013.01); *C07B 2200/05* (2013.01)

(58) Field of Classification Search
CPC .. C07D 498/06; C07D 471/06; C07B 59/002; C07B 2200/05
USPC ....................................................... 514/230.2
See application file for complete search history.

(56) References Cited

U.S. PATENT DOCUMENTS 9,227,985 B2 1/2016 Combs et al.
9,650,358 B2 5/2017 Mastracchio et al.
11,053,238 B2 7/2021 Wang et al.
11,111,233 B2 9/2021 Wang et al.
2019/0330196 A1 10/2019 Chen et al.

FOREIGN PATENT DOCUMENTS

CN 104903321 A 9/2015
CN 105164131 A 12/2015
CN 105189481 A 12/2015
CN 105294655 A 2/2016
CN 110234652 A 9/2019
CN 113698391 A 11/2021
WO 2016015604 A1 2/2016
WO 2018019204 A1 2/2018
WO 2019207463 A1 10/2019

OTHER PUBLICATIONS

Written Opinion of the International Searching Authority; China National Intellectual Property Administration; International Application No. PCT/CN2022/074509; mailed Apr. 26, 2022; 16 pages.
International Preliminary Report on Patentability; The International Bureau of WIPO; International Application No. PCT/CN2022/074509; issued Aug. 3, 2023; 17 pages.
Johnson et al., "Cyclins and Cell Cycle Checkpoints," Annu. Rev. Pharmacol. Toxicol., 1999, vol. 39, pp. 295-312.
Morgan, D., "Cyclin-Dependent Kinases: Engines, Clocks and Microprocessors," Annu. Rev. Cell Dev. Biol., 1997, vol. 13, pp. 261-291.
O'Leary et al., "Treating cancer with selective CDK4/6 inhibitors," Nature Reviews, 2016, vol. 13, pp. 417-430.
Sledge, Jr. et al., "Monarch 2: Abemaciclib in Combination With Fulvestrant in Women With HR+/HER2− Advanced Breast Cancer Who Had Progressed While Receiving Endocrine Therapy," J. Clin. Oncol., 2017, vol. 35, No. 25, pp. 2875-2884.
Malumbres et al., "Mammalian Cells Cycle without the D-Type Cyclin-Dependent Kinases Cdk4 and Cdk6," Cell, 2004, vol. 118, pp. 493-504.

(Continued)

*Primary Examiner* — Kahsay Habte
(74) *Attorney, Agent, or Firm* — Taft Stettinius & Hollister LLP

(57) ABSTRACT

Provided are a fused tricyclic cyclin-dependent kinase inhibitor, and a preparation method therefor and a pharmaceutical use thereof. In particular, the structure of the fused tricyclic cyclin-dependent kinase inhibitor is shown in formula I, wherein substituents are defined in the description. The fused tricyclic cyclin-dependent kinase inhibitor is used for preventing and/or treating cyclin-dependent kinase related diseases, in particular cancers.

I

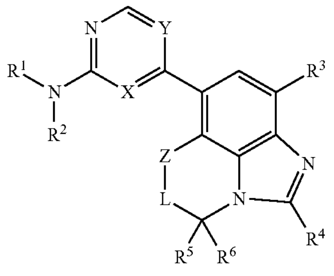

34 Claims, No Drawings

(56) References Cited

OTHER PUBLICATIONS

Sicinska et al., “Essential Role for Cyclin D3 in Granulocyte Colony-Stimulating Factor-Driven Expansion of Neutrophil Granulocytes,” Molecular and Cellular Biology, 2006, vol. 26, No. 21, pp. 8052-8060.
Cooper et al., “A unique function for cyclin D3 in early B cell development,” Nature Immunology, 2006, vol. 7, No. 5, pp. 489-497.
International Search Report; China National Intellectual Property Administration; International Application No. PCT/CN2022/074509; Apr. 26, 2022; 9 pages.
Xi et al.; Research progress of deuterated drugs; Tianjin Pharmacy; 2020; vol. 32; No. 1; pp. 44-56.

FUSED TRICYCLIC CYCLIN-DEPENDENT KINASE INHIBITOR, AND PREPARATION METHOD THEREFOR AND PHARMACEUTICAL USE THEREOF

CROSS-REFERENCE TO RELATED APPLICATIONS

This application is a U.S. National Phase of International PCT Application No. PCT/CN2022/074509 filed on Jan. 28, 2022, which claims priority to Chinese Patent Application Serial No. 202110152320.9 filed on Feb. 3, 2021, Chinese Patent Application Serial No. 202110342800.1 filed on Mar. 30, 2021, Chinese Patent Application Serial No. 202110485700.4 filed on Apr. 30, 2021, and Chinese Patent Application Serial No. 202110667137.2 filed on Jun. 16, 2021, the contents of each application are incorporated herein by reference in their entireties.

TECHNICAL FIELD

The present disclosure belongs to the field of pharmaceutics, and relates to a fused tricyclic cyclin-dependent kinase inhibitor and a preparation method therefor, a composition thereof and pharmaceutical use thereof.

BACKGROUND

Cyclin-dependent kinases (CDKs) are important cellular enzymes that play an important role in regulating eukaryotic cell division and proliferation. The cyclin-dependent kinase catalytic units are activated by regulatory subunits known as cyclins. At least 16 mammalian cyclins have been identified (*Annu. Rev. Pharmacol. Toxicol.* (1999) 39:295-312). Cyclin B/CDK1, cyclin A/CDK2, cyclin E/CDK2, cyclin D/CDK4, cyclin D/CDK6 and likely other heterodynes are important regulators of cell cycle progression. Additional functions of cyclin/CDK heterodynes include regulation of transcription, DNA repair, differentiation and apoptosis (*Annu. Rev. Cell. Dev. Biol.* (1997) 13:261-291).

In recent years, the greatest progress in the field of breast cancer therapy has undoubtedly been the use of CDK4/6 alone or in combination with endocrine therapy for hormone receptor positive advanced breast cancer. For example, palbociclib, ribociclib and abemaciclib have been approved for the treatment of hormone receptor (HR)-positive, human epidermal growth factor receptor 2 (HER2)-negative advanced or metastatic breast cancer in combination with aromatase inhibitors in post-menopausal women, and palbociclib and abemaciclib have been approved for the treatment of hormone receptor (HR)-positive, human epidermal growth factor receptor 2 (HER2)-negative advanced or metastatic breast cancer in combination with fulvestrant in post-menopausal women after disease progression following endocrine therapy (*Nature Reviews* (2016) 13:417-430; and *J Clin Oncol* 2017, 35, 2875-2884). While CDK4/6 inhibitors have shown significant clinical efficacy in ER-positive metastatic breast cancer, as with other kinases, their effects may be limited over time by the development of primary or acquired resistance.

Treatment with CDK4/6 inhibitors has been clinically shown to cause adverse reactions, such as gastrointestinal and/or hematologic toxicity, and acquired resistance may develop over time. Emerging data suggest that cyclin D3-CDK6 may be associated with the observed hematologic toxicity. (Malumbres et al., Mammalian Cells Cycle without the D-Type Cyclin-Dependent Kinases Cdk4 and Cdk6, (2004) Cell 118(4):493-504; Sicinska et al., Essential Role for Cyclin D3 in Granulocyte Colony-Stimulating Factor-Driven Expansion of Neutrophil Granulocytes (2006), Mol. Cell Biol 26(21):8052-8060; and Cooper et al., A unique function for cyclin D3 in early B cell development, (2006), Nat. Immunol. 5(7):489-497). CDK4 has been identified as the singular oncogenic driver in many breast cancers. Accordingly, CDK4 selective inhibitors can provide improved safety or enhanced overall efficacy due to the potential higher and/or continuous dosing compared to dual CDK4/6 inhibitors. Therefore, the development of molecules with high selectivity for CDK4 is of clinical practical value. WO2019207463A discloses a class of cyclin-dependent kinase inhibitors.

SUMMARY

The present disclosure provides a compound of formula I or a pharmaceutically acceptable salt thereof,

I

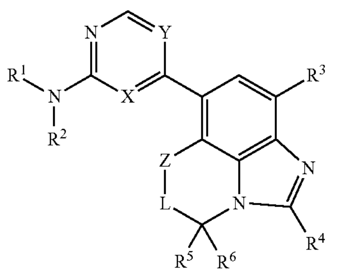

wherein $R^1$ is selected from the group consisting of H, $C_{1-6}$ alkyl, $C_{1-6}$ haloalkyl and $C_{3-8}$ cycloalkyl; the $C_{1-6}$ alkyl, $C_{1-6}$ haloalkyl and $C_{3-8}$ cycloalkyl are each independently and optionally substituted with one or more $R^a$;

$R^2$ is a structure of formula II:

II

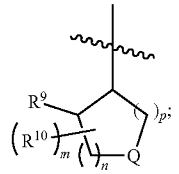

$R^9$ is selected from the group consisting of H, OH and $NH_2$; the $NH_2$ is optionally substituted with 1 or 2 $R^{a'}$ or $R^{a''}$;

each $R^{10}$ is independently selected from the group consisting of OH, halogen, CN, $NH_2$, $C_{1-6}$ alkyl, $C_{1-6}$ alkoxy, $C_{1-6}$ haloalkyl, $C_{1-6}$ haloalkoxy, $C_{3-8}$ cycloalkyl and 3-12 membered heterocycloalkyl; the $C_{1-6}$ alkyl, $C_{1-6}$ alkoxy, $C_{1-6}$ haloalkyl, $C_{3-8}$ cycloalkyl and 3-12 membered heterocycloalkyl are each independently and optionally substituted with one or more $R^b$;

Q is $NR^{11}$ or O;

or Q is $CR^{12}R^{13}$, wherein $R^{12}$ and $R^{13}$, together with the carbon atom to which they are attached, form a 3-12 membered heterocycloalkyl group containing N or O of $NR^{11}$ as a ring atom; the heterocycloalkyl group is optionally substituted with one or more $R^{10}$;

$R^{11}$ is selected from the group consisting of H, $C_{1-6}$ alkyl, $C_{1-6}$ haloalkyl, $SO_2R^c$, $SO_2NR^dR^e$, $COR^f$, $COOR^f$ and $CONR^gR^h$; the $C_{1-6}$ alkyl and $C_{1-6}$ haloalkyl are each independently and optionally substituted with one or more substituents selected from the group consisting of $R^a$, $R^b$, $SO_2R^c$, $SO_2NR^dR^e$, $COR^f$, $COOR^f$ and $CONR^gR^h$;

m is 0, 1 or 2;

n is 0, 1, 2, 3 or 4;

p is 1, 2 or 3;

X is N or CH;

Y is N or $CR^7$; $R^7$ is selected from the group consisting of H, F, Cl, CN, $C_{1-6}$ alkyl and $C_{1-6}$ alkoxy; the $C_{1-6}$ alkyl and $C_{1-6}$ alkoxy are each independently and optionally substituted with one or more $R^a$;

$R^3$ is selected from the group consisting of H, F, Cl, CN, $CH_2F$, $CHF_2$ and $CF_3$;

$R^4$ is selected from the group consisting of H, $C_{1-6}$ alkyl, $C_{1-6}$ alkoxy, $C_{3-8}$ cycloalkyl and 3-12 membered heterocycloalkyl; the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms;

Z is O or $CHR^8$; $R^8$ is selected from the group consisting of hydrogen, deuterium and halogen;

L is $-(CH_2)_q-$; the $-(CH_2)-$ is optionally substituted with one or more substituents selected from the group consisting of deuterium, CN, halogen, $C_{1-6}$ alkyl, $C_{3-8}$ cycloalkyl, $C_{1-6}$ alkoxy and 3-12 membered heterocycloalkyl; the $C_{1-6}$ alkyl, $C_{3-8}$ cycloalkyl, $C_{1-6}$ alkoxy and 3-12 membered heterocycloalkyl are each independently and optionally substituted with one or more $R^b$ or deuterium atoms;

q is 1, 2, 3 or 4;

$R^5$ and $R^6$ are each independently selected from the group consisting of H, deuterium, CN, halogen, $C_{1-6}$ alkyl, $C_{3-8}$ cycloalkyl, $C_{1-6}$ alkoxy and 3-12 membered heterocycloalkyl; the $C_{1-6}$ alkyl, $C_{3-8}$ cycloalkyl, $C_{1-6}$ alkoxy and 3-12 membered heterocycloalkyl are each optionally and independently substituted with one or more $R^b$ or deuterium atoms;

$R^a$ and $R^b$ are each independently selected from the group consisting of H, OH, CN, halogen (fluorine, chlorine, bromine or iodine), $C_{1-6}$ alkyl, $C_{1-6}$ alkoxy, $C_{1-6}$ haloalkyl, $C_{1-6}$ haloalkoxy, $C_{3-8}$ cycloalkyl, 3-12 membered heterocycloalkyl and $NR^{a'}R^{a''}$; the $C_{1-6}$ alkyl, $C_{1-6}$ alkoxy, $C_{1-6}$ haloalkyl, $C_{3-8}$ cycloalkyl and 3-12 membered heterocycloalkyl are each independently and optionally substituted with one or more substituents selected from the group consisting of $NH_2$, $NHCH_3$, $N(CH_3)_2$, halogen, OH, $C_{1-6}$ alkyl, $C_{1-6}$ alkoxy, $C_{1-6}$ haloalkyl, $C_{3-8}$ cycloalkyl and 3-12 membered heterocycloalkyl;

$R^{a'}$ and $R^{a''}$ are each independently selected from the group consisting of H, $C_{1-6}$ alkyl, $C_{1-6}$ haloalkyl, $C_{3-8}$ cycloalkyl and 3-12 membered heterocycloalkyl; the $C_{1-6}$ alkyl, $C_{1-6}$ haloalkyl, $C_{3-8}$ cycloalkyl and 3-12 membered heterocycloalkyl are each independently and optionally substituted with one or more substituents selected from the group consisting of $NH_2$, $NHCH_3$, $N(CH_3)_2$, halogen, OH, $C_{1-6}$ alkyl, $C_{1-6}$ alkoxy, $C_{1-6}$ haloalkyl, $C_{1-6}$ haloalkoxy, $C_{3-8}$ cycloalkyl and 3-12 membered heterocycloalkyl;

or $R^{a'}$ and $R^{a''}$, together with the N atom to which they are attached, form a 3-12 membered heterocycloalkyl group; the 3-12 membered heterocycloalkyl group is optionally substituted with one or more substituents selected from the group consisting of halogen, OH, $C_{1-6}$ alkyl, $C_{1-6}$ alkoxy, $C_{1-6}$ haloalkyl, $C_{1-6}$ haloalkoxy, $C_{3-8}$ cycloalkyl and 3-12 membered heterocycloalkyl;

$R^c$, $R^d$ and $R^e$ are each independently selected from the group consisting of H, $C_{1-6}$ alkyl, $C_{1-6}$ alkoxy, $C_{3-8}$ cycloalkyl and $C_{1-6}$ haloalkyl;

$R^f$ is selected from the group consisting of H, $C_{1-6}$ alkyl, $C_{1-6}$ haloalkyl, $C_{3-8}$ cycloalkyl and 3-12 membered heterocycloalkyl; the $C_{1-6}$ alkyl, $C_{1-6}$ haloalkyl, $C_{3-8}$ cycloalkyl and 3-12 membered heterocycloalkyl are each independently and optionally substituted with one or more substituents selected from the group consisting of $NH_2$, $NHCH_3$, $N(CH_3)_2$, halogen, OH, $C_{1-6}$ alkyl, $C_{1-6}$ alkoxy, $C_{1-6}$ haloalkyl, $C_{3-8}$ cycloalkyl and 3-12 membered heterocycloalkyl;

$R^g$ and $R^h$ are each independently selected from the group consisting of H, $C_{1-6}$ alkyl, $C_{1-6}$ alkoxy, $C_{1-6}$ haloalkyl and $C_{3-8}$ cycloalkyl; the $C_{1-6}$ alkoxy, $C_{1-6}$ haloalkyl and $C_{3-8}$ cycloalkyl are each independently and optionally substituted with one or more $R^a$ or $R^b$.

In an alternative embodiment, the present disclosure provides a compound of formula I or a pharmaceutically acceptable salt thereof, wherein $R^1$ is H or $C_{1-6}$ alkyl.

In an alternative embodiment, the present disclosure provides a compound of formula I or a pharmaceutically acceptable salt thereof, wherein $R^1$ is H.

In an alternative embodiment, the present disclosure provides a compound of formula I or a pharmaceutically acceptable salt thereof, wherein $R^2$ is selected from the group consisting of

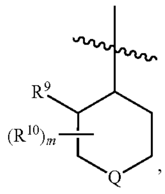
,
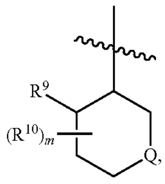
,
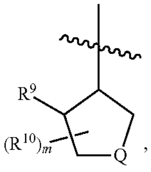
,
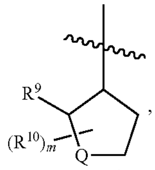
,
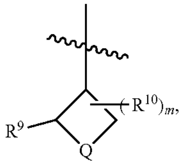
,
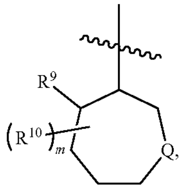
,
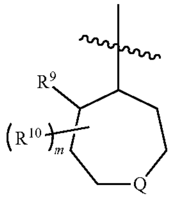
and
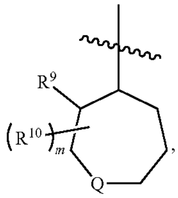
, wherein $R^9$, $R^{10}$, m and Q are as defined in the compound of formula I.

In an alternative embodiment, the present disclosure provides a compound of formula I or a pharmaceutically acceptable salt thereof, wherein $R^2$ is

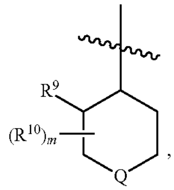

, wherein $R^9$, $R^{10}$, m and Q are as defined in the compound of formula I.

In an alternative embodiment, the present disclosure provides a compound of formula I or a pharmaceutically acceptable salt thereof, wherein $R^2$ is

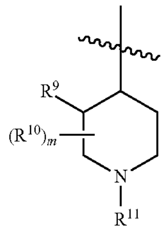

or

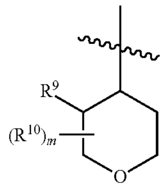

, wherein $R^9$, $R^{10}$, $R^{11}$ and m are as defined in the compound of formula I.

In an alternative embodiment, the present disclosure provides a compound of formula I or a pharmaceutically acceptable salt thereof, wherein $R^9$ is OH or $NH_2$; the $NH_2$ is optionally substituted with 1 or 2 $R^{a'}$ or $R^{a''}$; $R^{a'}$ and $R^{a''}$ are each independently $C_{1-6}$ alkyl.

In an alternative embodiment, the present disclosure provides a compound of formula I or a pharmaceutically acceptable salt thereof, wherein $R^9$ is OH.

In an alternative embodiment, the present disclosure provides a compound of formula I or a pharmaceutically acceptable salt thereof, wherein $R^9$ is $NH_2$.

In an alternative embodiment, the present disclosure provides a compound of formula I or a pharmaceutically acceptable salt thereof, wherein X is N.

In an alternative embodiment, the present disclosure provides a compound of formula I or a pharmaceutically acceptable salt thereof, wherein Y is $CR^7$; $R^7$ is selected from the group consisting of H, F, Cl and $C_{1-6}$ alkyl.

In an alternative embodiment, the present disclosure provides a compound of formula I or a pharmaceutically acceptable salt thereof, wherein $R^3$ is selected from the group consisting of H, F and Cl.

In an alternative embodiment, the present disclosure provides a compound of formula I or a pharmaceutically acceptable salt thereof, wherein $R^4$ is selected from the group consisting of H, $C_{1-6}$ alkyl, $C_{1-6}$ alkoxy, $C_{3-8}$ cycloalkyl and 3-12 membered heterocycloalkyl; the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms; $R^b$ is selected from the group consisting of H, OH, CN, halogen (fluorine, chlorine, bromine or iodine), $C_{1-6}$ alkyl, $C_{1-6}$ alkoxy, $C_{1-6}$ haloalkyl, $C_{1-6}$ haloalkoxy and $C_{3-8}$ cycloalkyl.

In an alternative embodiment, the present disclosure provides a compound of formula I or a pharmaceutically acceptable salt thereof, wherein $R^4$ is $C_{1-6}$ alkyl; the $C_{1-6}$ alkyl is optionally substituted with one or more $R^b$ or deuterium atoms; $R^b$ is selected from the group consisting of OH, CN, halogen (fluorine, chlorine, bromine or iodine), $C_{1-6}$ alkyl, $C_{1-6}$ alkoxy, $C_{1-6}$ haloalkyl, $C_{1-6}$ haloalkoxy and $C_{3-8}$ cycloalkyl.

In an alternative embodiment, the present disclosure provides a compound of formula I or a pharmaceutically acceptable salt thereof, wherein $R^4$ is $C_{1-6}$ alkyl; the $C_{1-6}$ alkyl is optionally substituted with one or more $R^b$ or deuterium atoms; $R^b$ is selected from the group consisting of OH, CN and halogen (fluorine, chlorine, bromine or iodine).

In an alternative embodiment, the present disclosure provides a compound of formula I or a pharmaceutically acceptable salt thereof, wherein L is $-(CH_2)_q-$; q is selected from the group consisting of 1 and 2; the $-(CH_2)-$ is optionally substituted with one or more substituents selected from the group consisting of deuterium, CN, halogen, $C_{1-6}$ alkyl, $C_{3-8}$ cycloalkyl, $C_{1-6}$ alkoxy and 3-12 membered heterocycloalkyl.

In an alternative embodiment, the present disclosure provides a compound of formula I or a pharmaceutically acceptable salt thereof, wherein L is $-(CH_2)_q-$; q is selected from 1; the $-(CH_2)-$ is optionally substituted with one or more substituents selected from the group consisting of deuterium, CN, halogen, $C_{1-6}$ alkyl, $C_{3-8}$ cycloalkyl, $C_{1-6}$ alkoxy and 3-12 membered heterocycloalkyl.

In an alternative embodiment, the present disclosure provides a compound of formula I or a pharmaceutically acceptable salt thereof, wherein L is $-(CH_2)_{qa}-$; q is selected from 1; the $-(CH_2)-$ is optionally substituted with one or more substituents of deuterium.

In an alternative embodiment, the present disclosure provides a compound of formula I or a pharmaceutically acceptable salt thereof, wherein $R^5$ and $R^6$ are each independently selected from the group consisting of H, deuterium, CN, halogen, $C_{1-6}$ alkyl and $C_{3-8}$ cycloalkyl.

In an alternative embodiment, the compound of formula I or the pharmaceutically acceptable salt thereof provided by the present disclosure is a compound of formula I-2 or a pharmaceutically acceptable salt thereof,

I-2

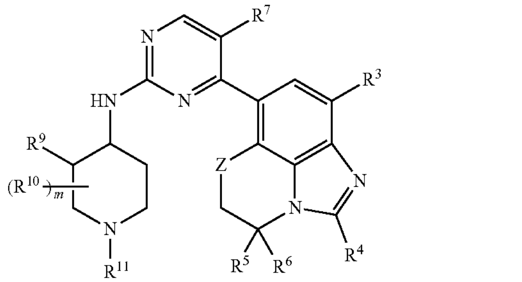

wherein $R^9$ is OH or $N_2$; the $NH_2$ is optionally substituted with 1 or 2 $R^{a'}$ or $R^{a''}$; $R^{a'}$ and $R^{a''}$ are each independently $C_{1-6}$ alkyl;

$R^{10}$ are each independently selected from the group consisting of H, OH, halogen, CN, $NH_2$, $C_{1-6}$ alkyl, $C_{1-6}$ alkoxy, $C_{1-6}$ haloalkyl and $C_{1-6}$ haloalkoxy;

m is 0, 1, or 2;

$R^{11}$ is selected from the group consisting of $SO_2R^c$, $SO_2NR^dR^e$, $COR^f$, $COOR^f$ and $CONR^gR^h$;

$R^c$, $R^d$ and $R^e$ are each independently selected from the group consisting of H, $C_{1-6}$ alkyl, $C_{1-6}$ alkoxy, $C_{3-8}$ cycloalkyl and $C_{1-6}$ haloalkyl;

$R^f$ is selected from the group consisting of H, $C_{1-6}$ alkyl, $C_{1-6}$ haloalkyl, $C_{3-8}$ cycloalkyl and 3-12 membered heterocycloalkyl;

$R^g$ and $R^h$ are each independently selected from the group consisting of H, $C_{1-6}$ alkyl, $C_{1-6}$ alkoxy, $C_{1-6}$ haloalkyl and $C_{3-8}$ cycloalkyl;

$R^7$ is selected from the group consisting of H, F, Cl and $C_{1-6}$ alkyl;

$R^3$ is selected from the group consisting of H, F and Cl;

$R^4$ is selected from the group consisting of H, $C_{1-6}$ alkyl, $C_{1-6}$ alkoxy, $C_{3-8}$ cycloalkyl and 3-12 membered heterocycloalkyl; the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms; $R^b$ is selected from the group consisting of H, OH, CN and halogen (fluorine, chlorine, bromine or iodine);

$R^5$ and $R^6$ are each independently selected from the group consisting of H, deuterium, CN, halogen, $C_{1-6}$ alkyl and $C_{3-8}$ cycloalkyl;

Z is O or $CHR^8$; $R^8$ is selected from the group consisting of hydrogen, deuterium and halogen.

In an alternative embodiment, the compound of formula I or the pharmaceutically acceptable salt thereof provided by the present disclosure is a compound of formula I-2 or a pharmaceutically acceptable salt thereof 2, wherein Z is O.

In an alternative embodiment, the compound of formula I or the pharmaceutically acceptable salt thereof provided by the present disclosure is a compound of formula I-2 or a pharmaceutically acceptable salt thereof, wherein Z is $CHR^8$; $R^8$ is selected from the group consisting of hydrogen, deuterium and halogen.

In an alternative embodiment, the compound of formula I or the pharmaceutically acceptable salt thereof provided by the present disclosure is a compound of formula I-2 or a pharmaceutically acceptable salt thereof, wherein $R^9$ is OH or $NH_2$; the $NH_2$ is optionally substituted with 1 or 2 $R^{a'}$ or $R^{a''}$; $R^{a'}$ and $R^{a''}$ are each independently $C_{1-6}$ alkyl;

m is 0;

$R^{11}$ is $SO_2R^c$;

$R^c$ is selected from the group consisting of H, $C_{1-6}$ alkyl and $C_{1-6}$ haloalkyl;

$R^7$ is selected from the group consisting of H, F, Cl and $C_{1-6}$ alkyl;

$R^3$ is selected from the group consisting of H, F and Cl;

$R^4$ is selected from the group consisting of H, $C_{1-6}$ alkyl and $C_{1-6}$ alkoxy; the $C_{1-6}$ alkyl and $C_{1-6}$ alkoxy are each independently and optionally substituted with one or more $R^b$ or deuterium atoms; $R^b$ is selected from the group consisting of H, OH, CN and halogen (fluorine, chlorine, bromine or iodine);

$R^5$ and $R^6$ are each independently selected from the group consisting of H, deuterium, CN, halogen and $C_{1-6}$ alkyl.

In an alternative embodiment, the compound of formula I or the pharmaceutically acceptable salt thereof provided by the present disclosure is a compound of formula I-2 or a pharmaceutically acceptable salt thereof, wherein $R^9$ is OH;

m is 0;

$R^{11}$ is $SO_2R^c$;

$R^c$ is $C_{1-6}$ alkyl or $C_{1-6}$ haloalkyl;

$R^7$ is F or Cl;

$R^3$ is F or Cl;

$R^4$ is H or $C_{1-6}$ alkyl, the $C_{1-6}$ alkyl is optionally substituted with one or more $R^b$ or deuterium atoms; $R^b$ is selected from the group consisting of H, OH, CN and halogen (fluorine, chlorine, bromine or iodine);

$R^5$ and $R^6$ are each independently H or $C_{1-6}$ alkyl.

In an alternative embodiment, the compound of formula I or the pharmaceutically acceptable salt thereof provided by the present disclosure is a compound of formula I-2 or a pharmaceutically acceptable salt thereof, wherein $R^9$ is OH;

m is 0;

$R^{11}$ is $SO_2R^c$;

$R^c$ is selected from the group consisting of methyl, ethyl, n-propyl, isopropyl, n-butyl, isobutyl and tert-butyl;

$R^7$ is F or Cl;

$R^3$ is F or Cl;

$R^4$ is H or $C_{1-6}$ alkyl, the $C_{1-6}$ alkyl is optionally substituted with one or more $R^b$ or deuterium atoms; $R^b$ is H or OH;

$R^5$ and $R^6$ are each independently selected from the group consisting of H, methyl, ethyl, n-propyl, isopropyl, n-butyl, isobutyl and tert-butyl.

In an alternative embodiment, the compound of formula I or the pharmaceutically acceptable salt thereof provided by the present disclosure is a compound of formula I-2 or a pharmaceutically acceptable salt thereof, wherein $R^9$ is OH;

m is 0;

$R^{11}$ is $SO_2R^c$;

$R^c$ is selected from the group consisting of methyl, ethyl and n-propyl;

$R^7$ is F or Cl;

$R^3$ is F or Cl;

$R^4$ is selected from the group consisting of H, methyl, ethyl, n-propyl, isopropyl, n-butyl, isobutyl and tert-butyl; the methyl, ethyl, n-propyl, isopropyl, n-butyl, isobutyl and tert-butyl are each independently and optionally substituted with one or more $R^b$; $R^b$ is H or OH;

$R^5$ and $R^6$ are each independently selected from the group consisting of H, methyl, ethyl, n-propyl, isopropyl, n-butyl, isobutyl and tert-butyl.

In an alternative embodiment, the compound of formula I or the pharmaceutically acceptable salt thereof provided by the present disclosure is a compound of formula I-2 or a pharmaceutically acceptable salt thereof, wherein $R^9$ is OH;

m is 0;

$R^{11}$ is $SO_2R^c$;

$R^c$ is methyl;

$R^7$ is F or Cl;

$R^3$ is F or Cl;

$R^4$ is selected from the group consisting of H, methyl, ethyl, n-propyl and isopropyl;

$R^5$ and $R^6$ are each independently selected from the group consisting of H, methyl, ethyl, n-propyl and isopropyl.

In an alternative embodiment, the compound of formula I or the pharmaceutically acceptable salt thereof provided by the present disclosure is a compound of formula I-3 or a pharmaceutically acceptable salt thereof,

I-3

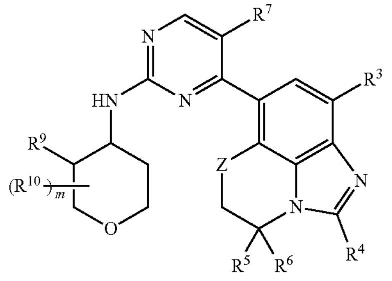

wherein $R^9$ is OH or $NH_2$; the $NH_2$ is optionally substituted with 1 or 2 $R^{a'}$ or $R^{a''}$; $R^{a'}$ and $R^{a''}$ are each independently $C_{1-6}$ alkyl;

$R^{10}$ are each independently selected from the group consisting of OH, halogen, CN, $NH_2$, $C_{1-6}$ alkyl, $C_{1-6}$ alkoxy, $C_{1-6}$ haloalkyl and $C_{1-6}$ haloalkoxy;

m is 0, 1, or 2;

$R^7$ is selected from the group consisting of H, F, Cl and $C_{1-6}$ alkyl;

$R^3$ is selected from the group consisting of H, F and Cl;

$R^4$ is selected from the group consisting of H, $C_{1-6}$ alkyl, $C_{1-6}$ alkoxy, $C_{3-8}$ cycloalkyl and 3-12 membered heterocycloalkyl; the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms; $R^b$ is selected from the group consisting of H, OH, CN and halogen (fluorine, chlorine, bromine or iodine);

$R^5$ and $R^6$ are each independently selected from the group consisting of H, deuterium, CN, halogen, $C_{1-6}$ alkyl and $C_{3-8}$ cycloalkyl;

Z is O or $CHR^8$; $R^8$ is selected from the group consisting of hydrogen, deuterium and halogen.

In an alternative embodiment, the compound of formula I or the pharmaceutically acceptable salt thereof provided by the present disclosure is a compound of formula I-3 or a pharmaceutically acceptable salt thereof, wherein Z is O.

In an alternative embodiment, the compound of formula I or the pharmaceutically acceptable salt thereof provided by the present disclosure is a compound of formula I-3 or a pharmaceutically acceptable salt thereof, wherein Z is $CHR^8$; $R^8$ is hydrogen, deuterium or halogen.

In an alternative embodiment, the compound of formula I or the pharmaceutically acceptable salt thereof provided by the present disclosure is a compound of formula I-3 or a pharmaceutically acceptable salt thereof, wherein $R^9$ is OH or $NH_2$; the $NH_2$ is optionally substituted with 1 or 2 $R^{a'}$ or $R^{a''}$; $R^{a'}$ and $R^{a''}$ are each independently $C_{1-6}$ alkyl;

m is 0;

$R^7$ is selected from the group consisting of H, F, Cl and $C_{1-6}$ alkyl;

$R^3$ is selected from the group consisting of H, F and Cl;

$R^4$ is selected from the group consisting of H, $C_{1-6}$ alkyl and $C_{1-6}$ alkoxy; the $C_{1-6}$ alkyl and $C_{1-6}$ alkoxy are each independently and optionally substituted with one or more $R^b$ or deuterium atoms; $R^b$ is selected from the group consisting of H, OH, CN and halogen (fluorine, chlorine, bromine or iodine);

$R^5$ and $R^6$ are each independently selected from the group consisting of H, deuterium, CN, halogen and $C_{1-6}$ alkyl.

In an alternative embodiment, the compound of formula I or the pharmaceutically acceptable salt thereof provided by the present disclosure is a compound of formula I-3 or a pharmaceutically acceptable salt thereof, wherein $R^9$ is OH;

m is 0;

$R^7$ is F or Cl;

$R^3$ is F or Cl;

$R^4$ is H or $C_{1-6}$ alkyl, the $C_{1-6}$ alkyl is optionally substituted with one or more $R^b$ or deuterium atoms; $R^b$ is selected from the group consisting of H, OH, CN and halogen (fluorine, chlorine, bromine or iodine);

$R^5$ and $R^6$ are each independently H or $C_{1-6}$ alkyl.

In an alternative embodiment, the compound of formula I or the pharmaceutically acceptable salt thereof provided by the present disclosure is a compound of formula I-3 or a pharmaceutically acceptable salt thereof, wherein $R^9$ is OH;

m is 0;

$R^7$ is F or Cl;

$R^3$ is F or Cl;

$R^4$ is H or $C_{1-6}$ alkyl, the $C_{1-6}$ alkyl is optionally substituted with one or more $R^b$ or deuterium atoms; $R^b$ is H or OH;

$R^5$ and $R^6$ are each independently selected from the group consisting of H, methyl, ethyl, n-propyl, isopropyl, n-butyl, isobutyl and tert-butyl.

In an alternative embodiment, the compound of formula I or the pharmaceutically acceptable salt thereof provided by the present disclosure is a compound of formula I-3 or a pharmaceutically acceptable salt thereof, wherein $R^9$ is OH;

m is 0;

$R^7$ is F or Cl;

$R^3$ is F or Cl;

$R^4$ is selected from the group consisting of H, methyl, ethyl, n-propyl, isopropyl, n-butyl, isobutyl and tert-butyl; the methyl, ethyl, n-propyl, isopropyl, n-butyl, isobutyl and tert-butyl are each independently and optionally substituted with one or more $R^b$; $R^b$ is H or OH;

$R^5$ and $R^6$ are each independently selected from the group consisting of H, methyl, ethyl, n-propyl, isopropyl, n-butyl, isobutyl and tert-butyl.

In an alternative embodiment, the compound of formula I or the pharmaceutically acceptable salt thereof provided by the present disclosure is a compound of formula I-3 or a pharmaceutically acceptable salt thereof, wherein $R^9$ is OH;

m is 0;

$R^7$ is F or Cl;

$R^3$ is F or Cl;

$R^4$ is selected from the group consisting of H, methyl, ethyl, n-propyl and isopropyl;

$R^5$ and $R^6$ are each independently selected from the group consisting of H, methyl, ethyl, n-propyl and isopropyl.

In an alternative embodiment, the compound of formula I or the pharmaceutically acceptable salt thereof provided by the present disclosure is selected from the group consisting of

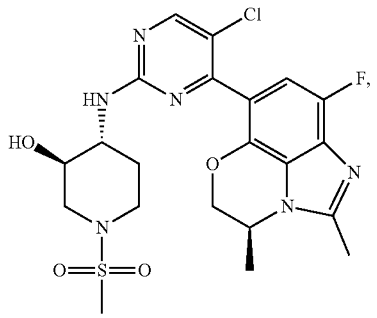
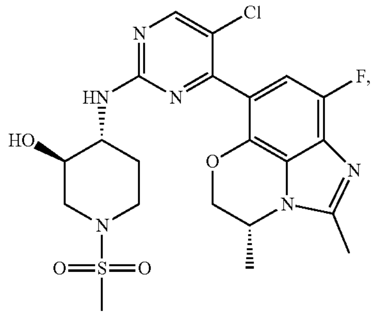
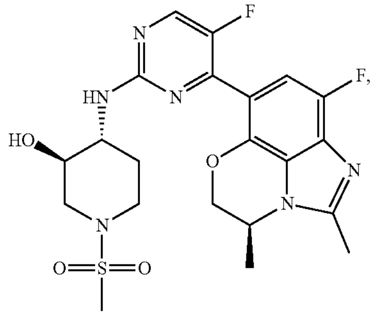
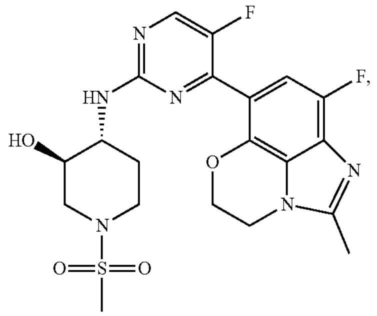
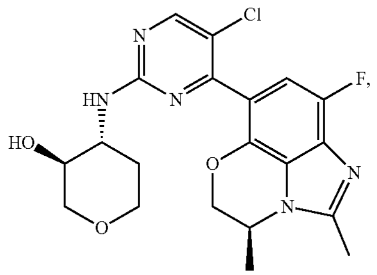
-continued
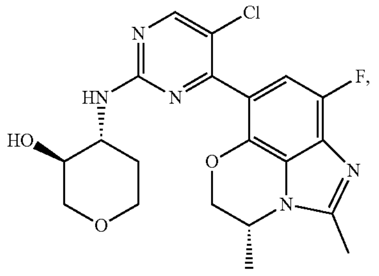
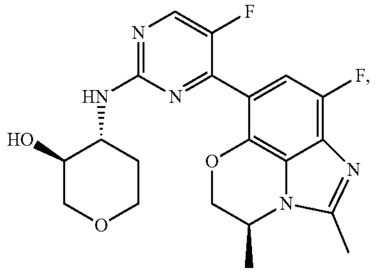
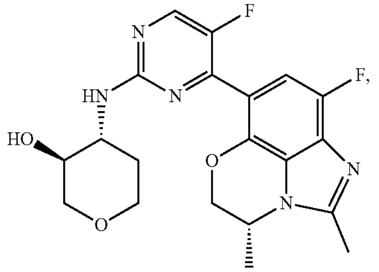
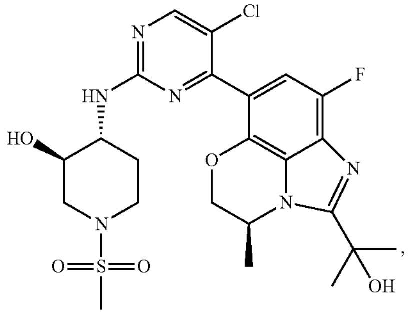
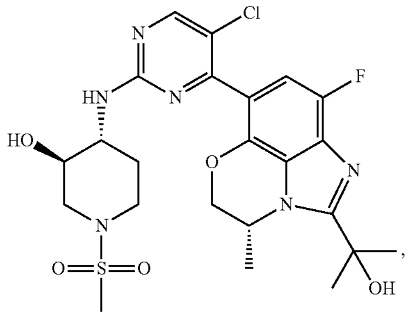

-continued
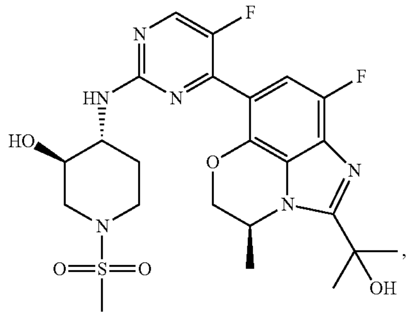
,
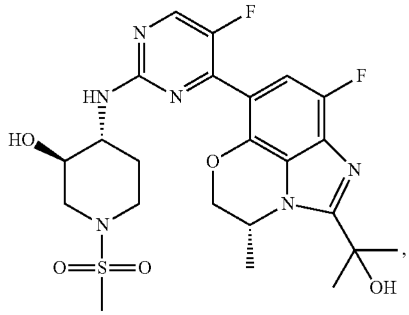
,
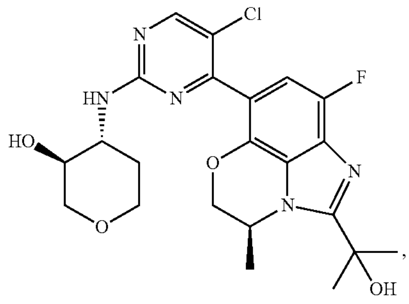
,
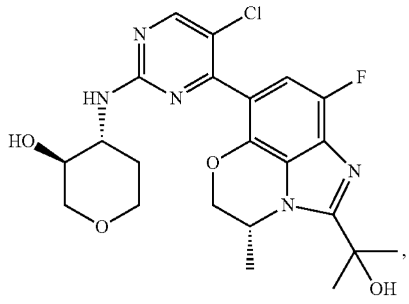
,
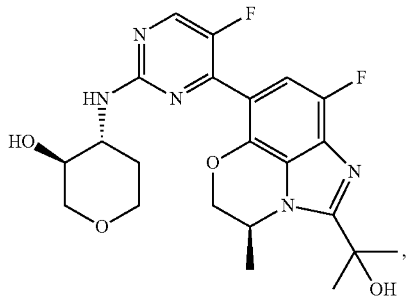
,
-continued
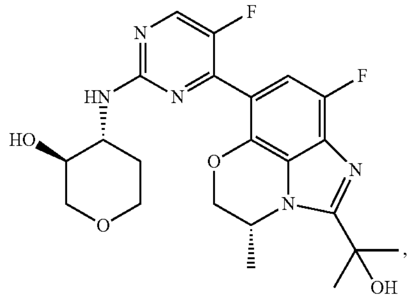
,
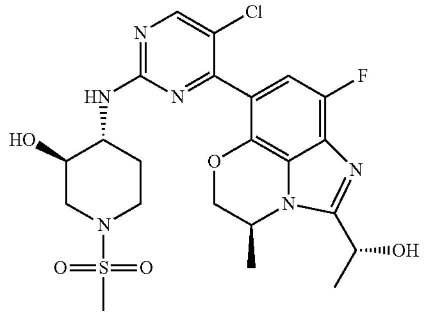
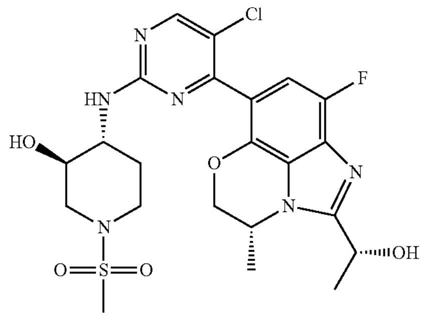
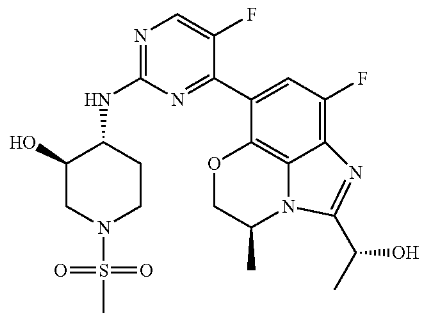
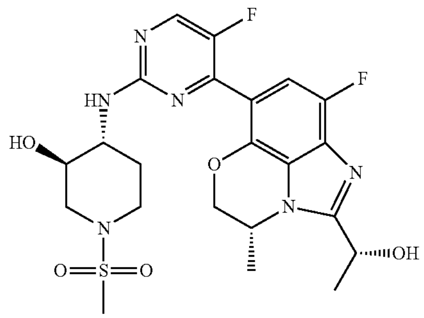

-continued
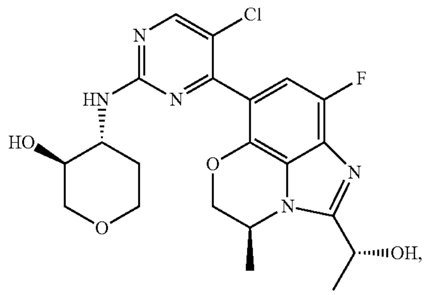
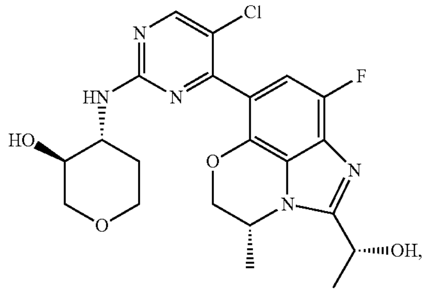
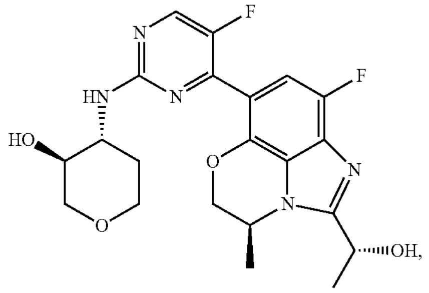
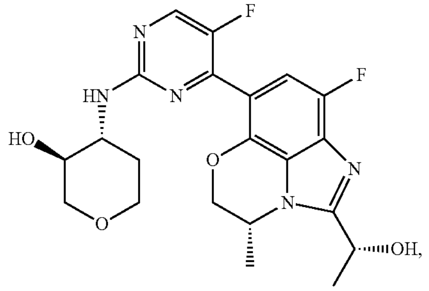
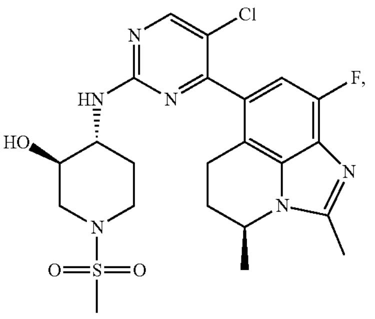
-continued
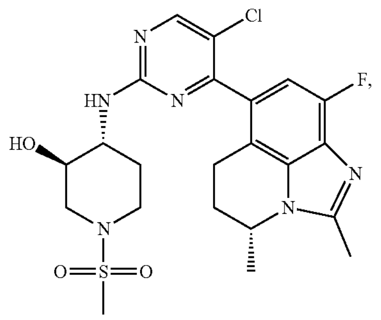
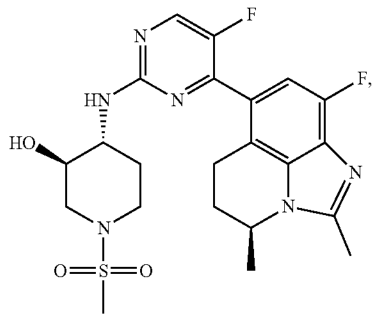
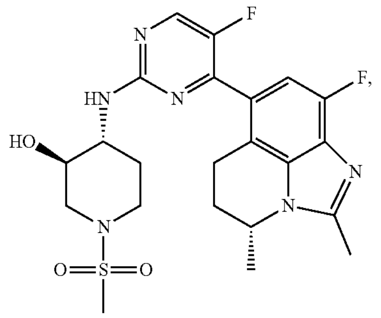
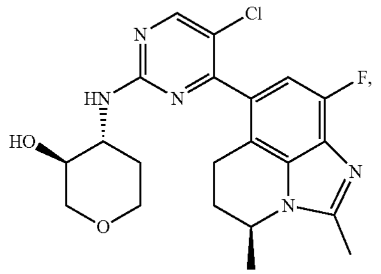
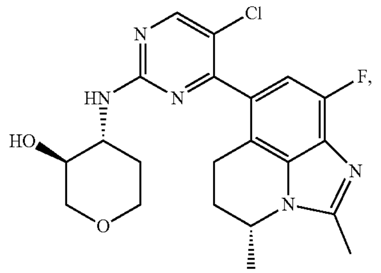

-continued
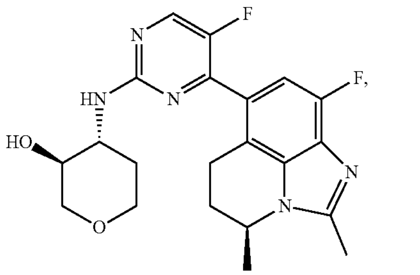
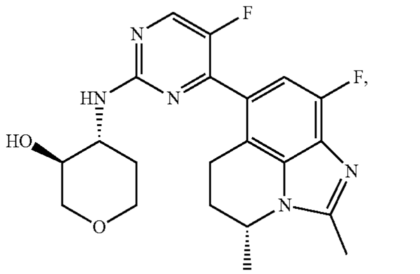
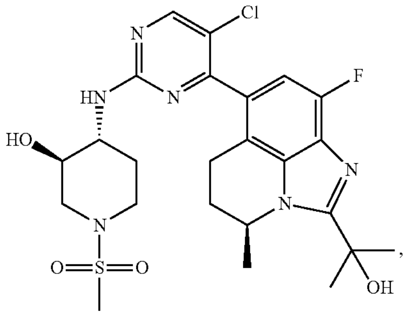
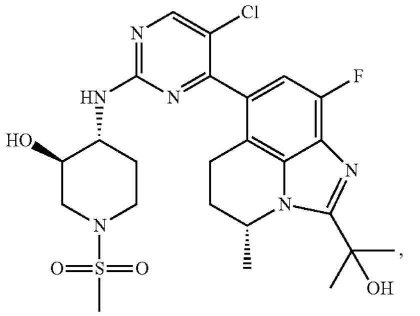
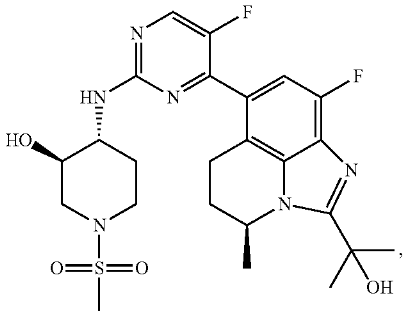
-continued
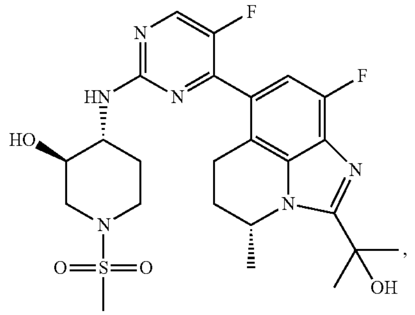
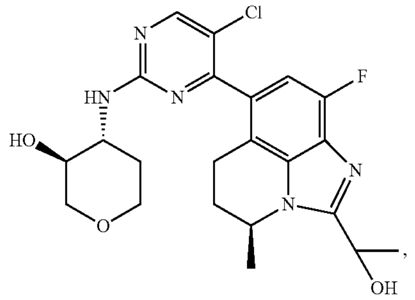
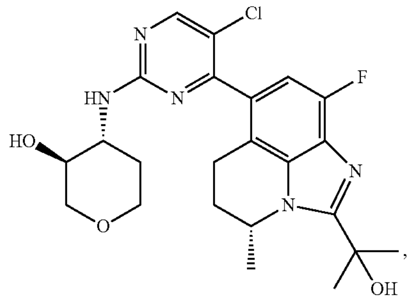
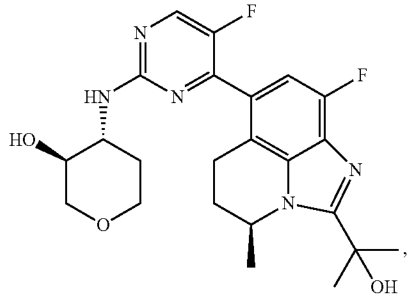
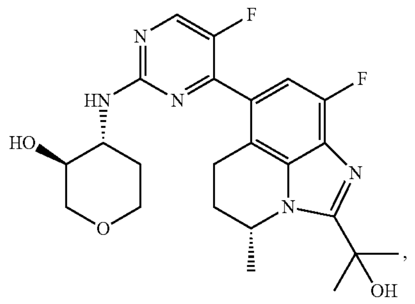

-continued
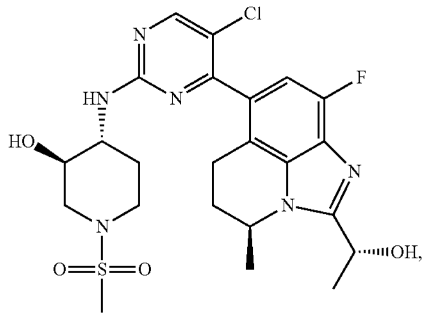
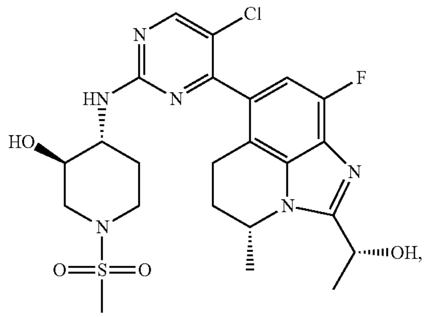
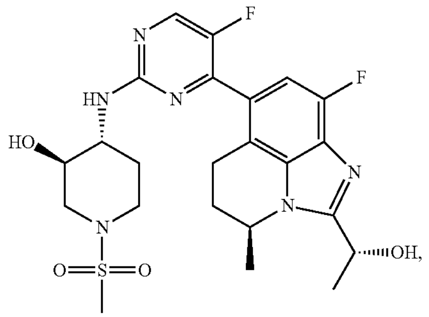
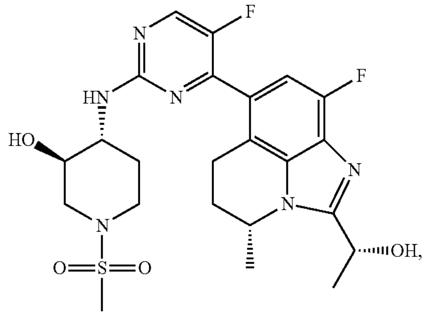
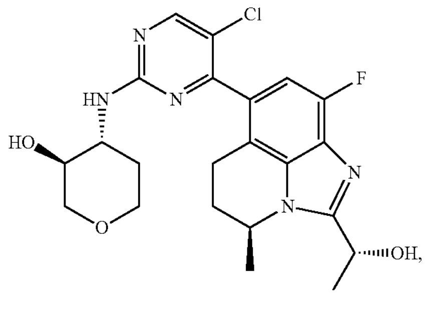
-continued
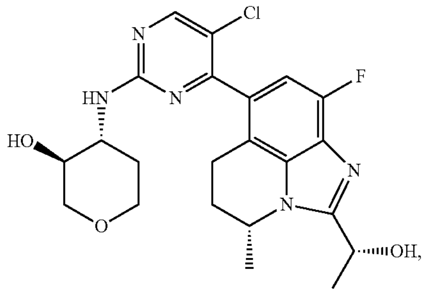
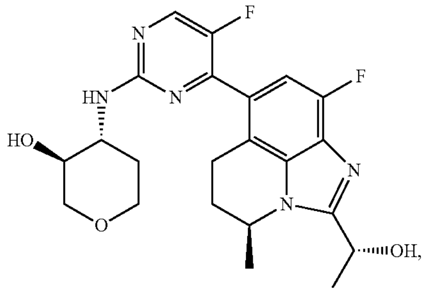
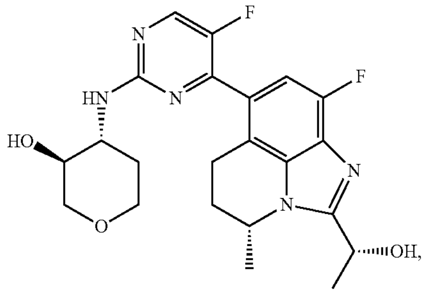
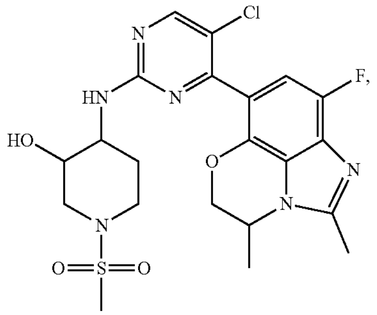
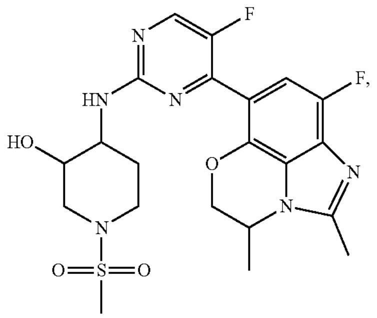

-continued
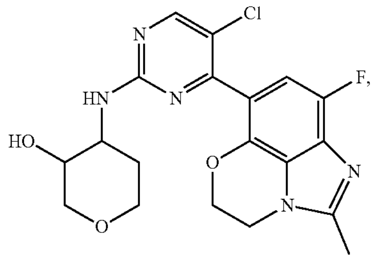
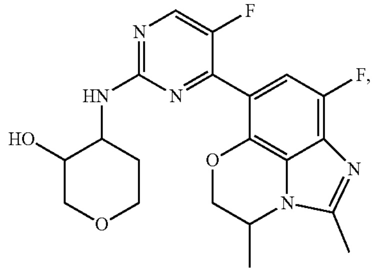
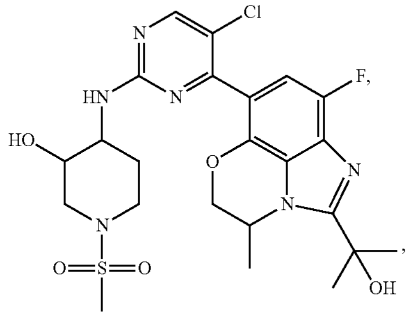
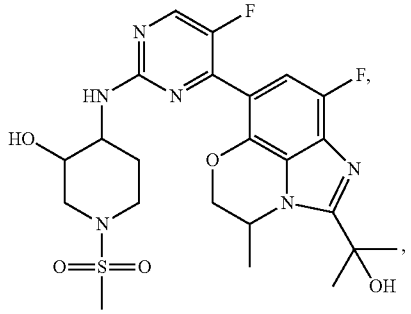
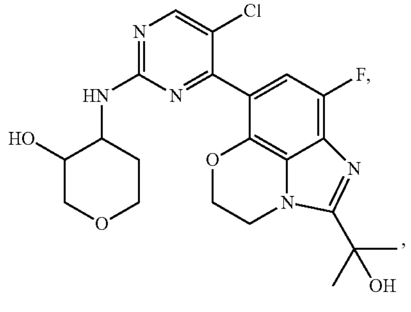
-continued
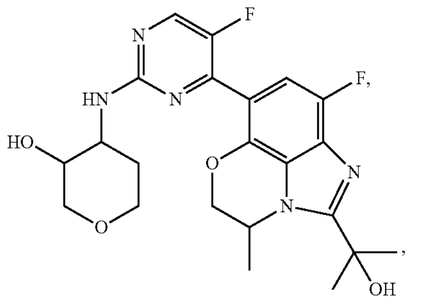
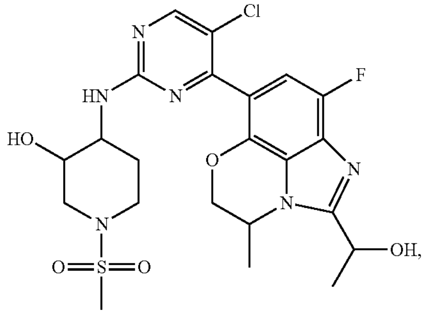
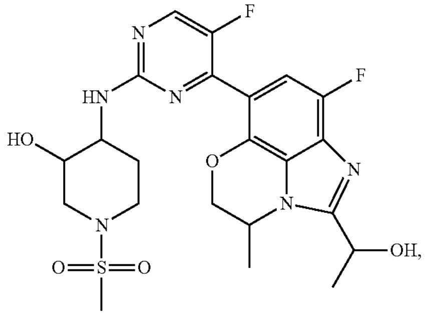
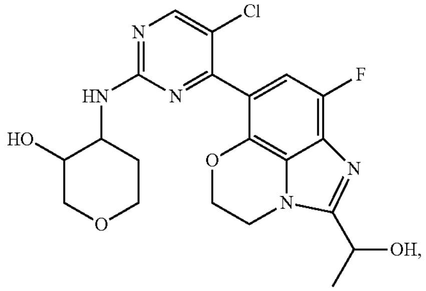
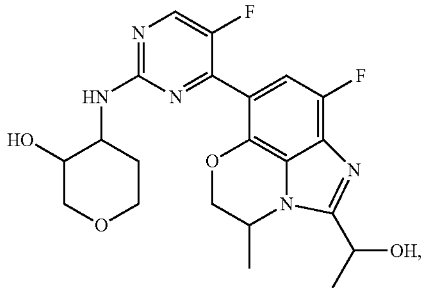

-continued
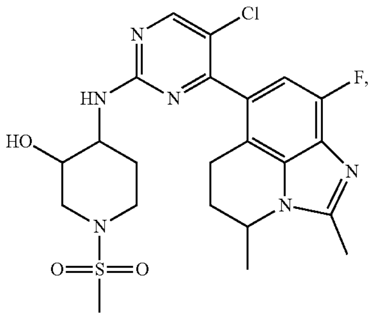
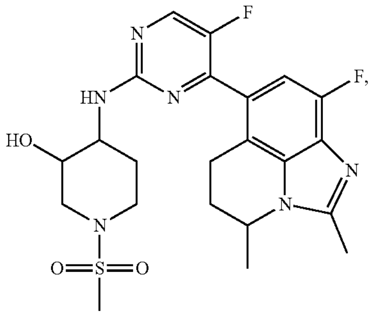
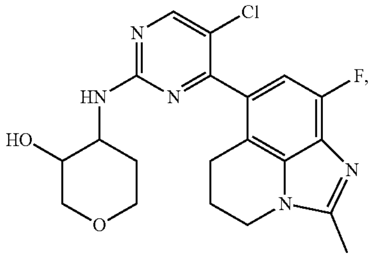
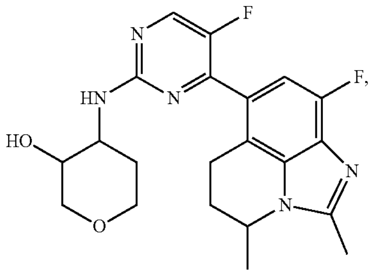
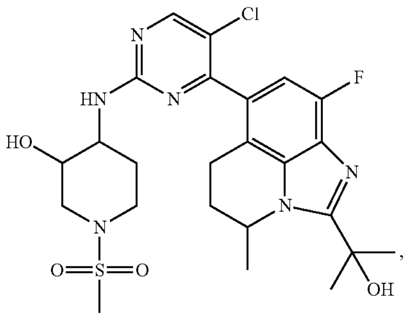
-continued
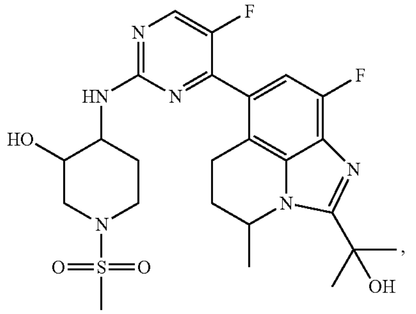
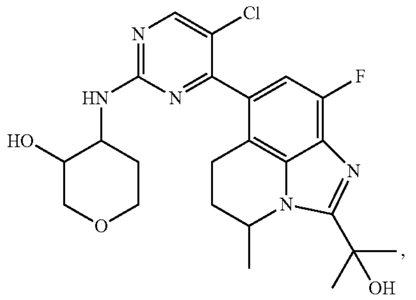
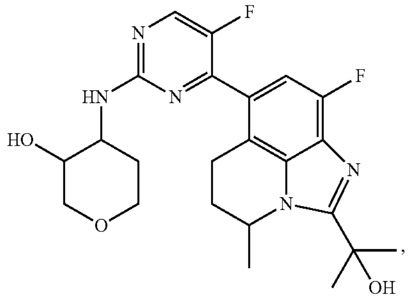
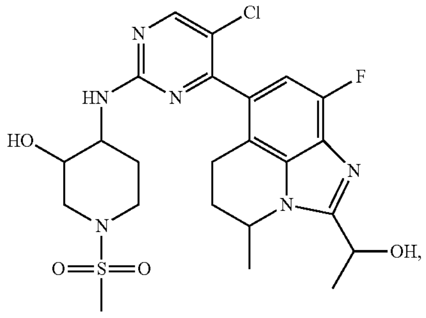
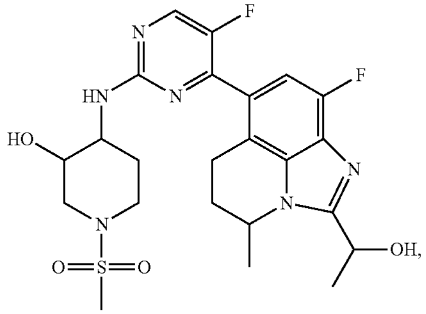

-continued

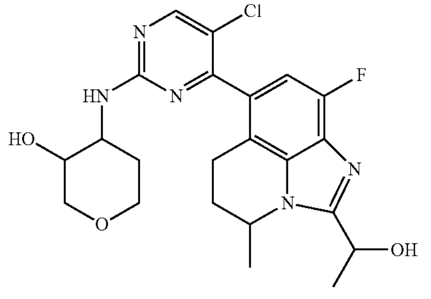

and

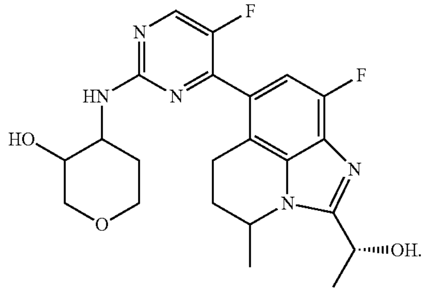

Another aspect of the present disclosure provides an isotopically substituted form of the compound of formula I, I-2 or I-3 or the pharmaceutically acceptable salt thereof described above. In an alternative embodiment, the isotopically substituted form is a deuterated form.

In an alternative embodiment, in the compound of formula I or the pharmaceutically acceptable salt thereof, the deuterium atom has an abundance of greater than 20%.

In an alternative embodiment, in the compound of formula I or the pharmaceutically acceptable salt thereof, the deuterium atom has an abundance of greater than 50%.

In an alternative embodiment, in the compound of formula I or the pharmaceutically acceptable salt thereof, the deuterium atom has an abundance of greater than 90%.

In an alternative embodiment, in the compound of formula I or the pharmaceutically acceptable salt thereof, the deuterium atom has an abundance of greater than 95%.

The present disclosure also provides a method for preparing the compound of formula I, which comprises a step of reacting a compound of formula I-B with a compound of formula I-C to form the compound of formula I,

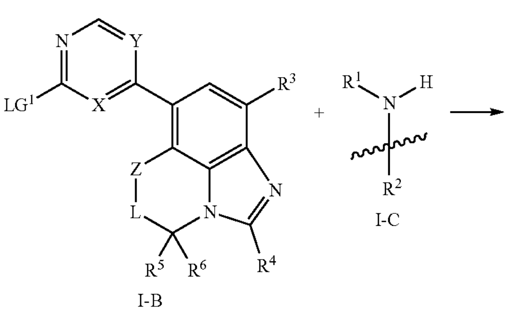

I-B

I-C

-continued

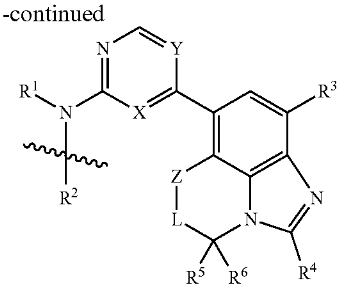

I wherein $LG^1$ is a leaving group; the leaving group is preferably halogen, sulfonate, boronic acid and borate; X, Y, Z, L, $R^1$, $R^2$, $R^3$, $R^4$, $R^5$ and $R^6$ are as defined in the compound of formula I.

In some embodiments, the reaction is carried out in the presence of a catalyst; the catalyst is the metal palladium or the metal nickel.

In some embodiments, the catalyst is selected from the group consisting of palladium/carbon, Raney Ni, tetrakis (triphenylphosphine)palladium(0), palladium dichloride, palladium acetate, [1,1'-bis(diphenylphosphino)ferrocene] palladium(II) dichloride, 1,1'-[1,1'-bis(di-tert-butylphosphino)ferrocene]palladium(II) dichloride, tris(dibenzylideneacetone)dipalladium(0) and 2-dicyclohexylphosphino-2',6'-dimethoxybiphenyl, preferably [1,1'-bis (diphenylphosphino)ferrocene]palladium(II) dichloride and 2-dicyclohexylphosphino-2',6'-dimethoxybiphenyl.

Another aspect of the present disclosure provides a compound of formula I-B or a pharmaceutically acceptable salt thereof,

I-B

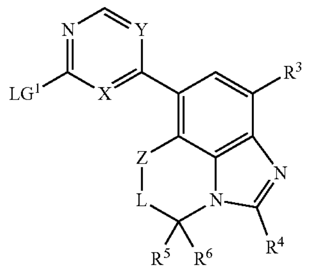

wherein $LG^1$ is a leaving group selected from the group consisting of halogen, sulfonate, boronic acid and borate; X, Y, Z, L, $R^3$, $R^4$, $R^5$ and $R^6$ are as defined in the compound of formula I.

The present disclosure also provides a pharmaceutical composition comprising a therapeutically effective amount of at least one of the compounds of formulas I, I-2 and I-3 or the pharmaceutically acceptable salts thereof described above or the isotopically substituted forms described above, and a pharmaceutically acceptable excipient.

In some embodiments, a unit dose of the pharmaceutical composition is 0.001 mg-1000 mg.

In certain embodiments, the pharmaceutical composition comprises 0.01-99.99% of the compound of formula I, I-2 or I-3 or the pharmaceutically acceptable salt thereof described above or the isotopically substituted form described above based on the total weight of the composition.

In certain embodiments, the pharmaceutical composition comprises 0.1-99.9% of the compound of formula I, I-2 or I-3 or the pharmaceutically acceptable salt thereof described above or the isotopically substituted form described above.

In certain embodiments, the pharmaceutical composition comprises 0.5%-99.5% of the compound of formula I, I-2 or I-3 or the pharmaceutically acceptable salt thereof described above or the isotopically substituted form described above.

In certain embodiments, the pharmaceutical composition comprises 1%-99% of the compound of formula I, I-2 or I-3 or the pharmaceutically acceptable salt thereof described above or the isotopically substituted form described above.

In certain embodiments, the pharmaceutical composition comprises 2%-98% of the compound of formula I, I-2 or I-3 or the pharmaceutically acceptable salt thereof described above or the isotopically substituted form described above.

In certain embodiments, the pharmaceutical composition comprises 0.01%-99.99% of a pharmaceutically acceptable excipient based on the total weight of the composition.

In certain embodiments, the pharmaceutical composition comprises 0.1%-99.9% of a pharmaceutically acceptable excipient.

In certain embodiments, the pharmaceutical composition comprises 0.5%-99.5% of a pharmaceutically acceptable excipient.

In certain embodiments, the pharmaceutical composition comprises 1%-99% of a pharmaceutically acceptable excipient.

In certain embodiments, the pharmaceutical composition comprises 2%-98% of a pharmaceutically acceptable excipient.

The present disclosure also provides a method for preventing and/or treating a cyclin-dependent kinase-associated disease, which comprises administering to a patient in need thereof a therapeutically effective amount of the compound of formula I, I-2 or I-3 or the pharmaceutically acceptable salt thereof described above or the isotopically substituted form described above, or the pharmaceutical composition described above.

The present disclosure also provides a method for preventing and/or treating cancer, which comprises administering to a patient in need thereof a therapeutically effective amount of the compound of formula I, I-2 or I-3 or the pharmaceutically acceptable salt thereof described above or the isotopically substituted form described above, or the pharmaceutical composition described above.

The present disclosure also provides use of the compound of formula I, I-2 or I-3 or the pharmaceutically acceptable salt thereof described above or the isotopically substituted form described above, or the pharmaceutical composition described above in the preparation of a medicament for preventing and/or treating a cyclin-dependent kinase-associated disease.

The present disclosure also provides use of the compound of formula I, I-2 or I-3 or the pharmaceutically acceptable salt thereof described above or the isotopically substituted form described above, or the pharmaceutical composition described above in the preparation of a medicament for preventing and/or treating cancer.

In an alternative embodiment, the cyclin-dependent kinase-associated disease is selected from the group consisting of a cell proliferation disease, cancer and an immune disease.

The cancer in the present disclosure is selected from the group consisting of breast cancer, ovarian cancer, bladder cancer, uterine cancer, prostate cancer, lung cancer (including NSCLC, SCLC, squamous cell carcinoma or adenocarcinoma), esophageal cancer, head and neck cancer, intestinal cancer, kidney cancer (including RCC), liver cancer (including HCC), pancreatic cancer, gastric cancer and thyroid cancer.

In an alternative embodiment, the cyclin-dependent kinase in the present disclosure is CDK4.

Another aspect of the present disclosure provides use of the compound of formula I, I-2 or I-3 or the pharmaceutically acceptable salt thereof described above or the isotopically substituted form described above as a medicament.

The compound of formulas I, I-2 or I-3 or the pharmaceutically acceptable salt thereof described above or the isotopically substituted form described above, or the pharmaceutical composition described above provided by the present disclosure reduces gastrointestinal and/or hematologic toxicity.

In another aspect, the pharmaceutically acceptable salt of the compound in the present disclosure is an inorganic or organic salt.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomer, (L)-isomer, and racemic mixtures and other mixtures thereof, such as enantiomerically or diastereomerically enriched mixtures, all of which are within the scope of the present disclosure. Additional asymmetric carbon atoms may be present in substituents such as an alkyl group. All such isomers and mixtures thereof are included within the scope of the present disclosure. The compounds of the present disclosure containing asymmetric carbon atoms can be isolated in optically active pure form or in racemic form. The optically active pure form can be isolated from a racemic mixture or synthesized using chiral starting materials or chiral reagents.

Optically active (R)- and (S)-enantiomers, and D- and L-isomers can be prepared by chiral synthesis, chiral reagents or other conventional techniques. If one enantiomer of a certain compound of the present disclosure is desired, it may be prepared by asymmetric synthesis or derivatization with a chiral auxiliary, wherein the resulting mixture of diastereomers is separated and the auxiliary group is cleaved to provide the pure desired enantiomer. Alternatively, when the molecule contains a basic functional group (e.g., amino) or an acidic functional group (e.g., carboxyl), salts of diastereomers are formed with an appropriate optically active acid or base, followed by resolution of diastereomers by conventional methods known in the art, and the pure enantiomers are obtained by recovery. Furthermore, separation of enantiomers and diastereomers is typically accomplished by chromatography using a chiral stationary phase, optionally in combination with chemical derivatization (e.g., carbamate formation from amines).

In the chemical structure of the compound of the present disclosure, a bond “ ” represents an unspecified configuration—that is, if chiral isomers exist in the chemical structure, the bond “ ” may be “ ” or “ ”, or contains both the configurations of “ ” and “ ”. The bond “ ” represents an unspecified configuration, including a cis (E) or trans (Z) configuration.

The compounds and intermediates of the present disclosure may also exist in different tautomeric forms, and all such forms are included within the scope of the present disclosure. The term “tautomer” or “tautomeric form” refers to structural isomers of different energies that can interconvert via a low energy barrier. For example, proton tautomers (also known as proton transfer tautomers) include interconversion via proton migration, such as keto-enol and imine-enamine, lactam-lactim isomerization. An example of a lactam-lactim equilibrium is present between A and B as shown below.

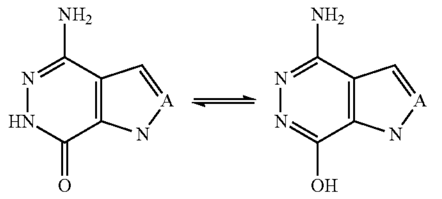

A B

All compounds in the present disclosure can be drawn as form A or form B. All tautomeric forms are within the scope of the present disclosure. The nomenclature of the compounds does not exclude any tautomers.

The present disclosure also comprises isotopically-labeled compounds which are identical to those recited herein but have one or more atoms replaced by an atom having an atomic mass or mass number different from the atomic mass or mass number usually found in nature. Examples of isotopes that can be incorporated into the compound of the present disclosure include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Unless otherwise specified, when a position is specifically assigned deuterium (D), the position should be construed as deuterium with an abundance that is at least 1000 times greater than the natural abundance of deuterium (which is 0.015%) (i.e., at least 10% deuterium incorporation). The compounds of examples comprise deuterium having an abundance that is greater than at least 1000 times the natural abundance, at least 2000 times the natural abundance, at least 3000 times the natural abundance, at least 4000 times the natural abundance, at least 5000 times the natural abundance, at least 6000 times the natural abundance, or higher times the natural abundance. The present disclosure also comprises various deuterated forms of the compound of formula (I). Each available hydrogen atom connected to a carbon atom may be independently replaced with a deuterium atom. Those skilled in the art are able to synthesize the deuterated forms of the compound of formula (I) with reference to the relevant literature. Commercially available deuterated starting materials can be used in preparing the deuterated forms of the compound of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like.

Terms and Definitions

"Pharmaceutically acceptable excipient" includes, but is not limited to, any adjuvant, carrier, excipient, glidant, sweetener, diluent, preservative, dye/colorant, flavoring agent, surfactant, wetting agent, dispersant, suspending agent, stabilizer, isotonic agent, solvent or emulsifier that has been approved by the U.S. food and drug administration as acceptable for use in humans or livestock animals.

"Alkyl" refers to a saturated aliphatic hydrocarbon group, including linear and branched groups of 1 to 20 carbon atoms, preferably alkyl having 1 to 12 carbon atoms, and more preferably alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl and various branched isomers thereof, and the like. The alkyl may be substituted or unsubstituted, and when it is substituted, the substituent may be substituted at any available point of attachment, and the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

"Alkenyl" includes branched and linear alkenyl having 2 to 12 carbon atoms or alkenyl containing aliphatic hydrocarbon groups. For example, "$C_{2-6}$ alkenyl" refers to an alkenyl group having 2, 3, 4, 5 or 6 carbon atoms. Examples of alkenyl include, but are not limited to, ethenyl, allyl, 1-propenyl, 1-butenyl, 2-butenyl, 3-butenyl, 2-methylbut-2-enyl, 3-methylbut-1-enyl, 1-pentenyl, 3-pentenyl, and 4-hexenyl. The alkenyl may be substituted or unsubstituted, and when it is substituted, the substituent may be substituted at any available point of attachment, and the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

"Alkynyl" includes branched and linear alkynyl having 2 to 12 carbon atoms or alkynyl containing aliphatic hydrocarbon groups, or alkynyl having a particular number of carbon atoms (if the particular number is specified), e.g., ethynyl, propynyl (e.g., 1-propynyl, 2-propynyl), 3-butynyl, pentynyl, hexynyl and 1-methylpent-2-ynyl. The alkynyl may be substituted or unsubstituted, and when it is substituted, the substituent may be substituted at any available point of attachment, and the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The cycloalkyl ring may be fused to an aryl, heteroaryl or heterocycloalkyl ring, wherein the ring attached to the parent structure is cycloalkyl; non-limiting examples include indanyl, tetrahydronaphthyl, benzocycloheptyl, and the like. The cycloalkyl may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

The term "heterocyclyl", also referred to as heterocycloalkyl, refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen and $S(O)_m$ (where m is an integer of 0 to 2), excluding a ring moiety of —O—O—, —O—S— or —S—

S—, and the remaining ring atoms are carbon atoms. The heterocyclyl preferably contains 3 to 12 ring atoms, of which 1 to 4 are heteroatoms; and more preferably contains 3 to 8 ring atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, etc. Polycyclic heterocyclyl includes spiro heterocyclyl, fused heterocyclyl, and bridged heterocyclyl. Non-limiting examples of "heterocyclyl" include:

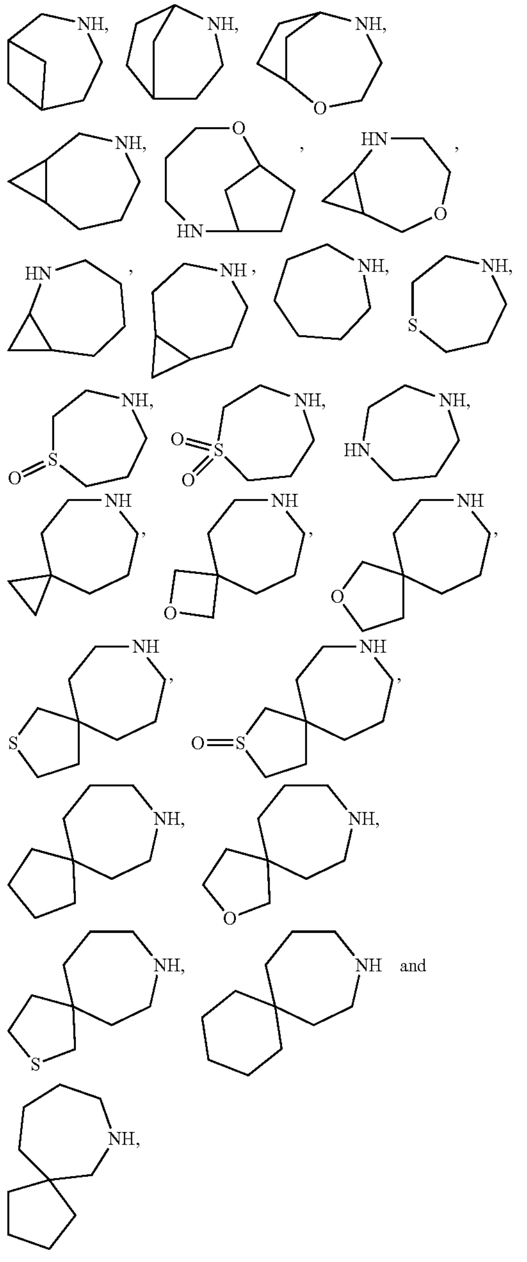

and the like.

The heterocyclyl ring may be fused to an aryl, heteroaryl or cycloalkyl ring, wherein the ring linked to the parent structure is heterocyclyl; its non-limiting examples include:

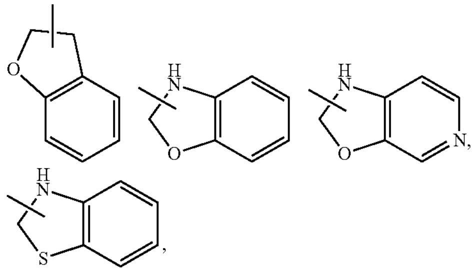

etc.

The heterocyclyl may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

The term "aryl" refers to a 6- to 14-membered, preferably 6- to 12-membered, carbon monocyclic or fused polycyclic (i.e., rings sharing a pair of adjacent carbon atoms) group having a conjugated π-electron system, such as phenyl and naphthyl. The aryl ring may be fused to a heteroaryl, heterocyclyl or cycloalkyl ring, wherein the ring linked to the parent structure is the aryl ring; its non-limiting examples include:

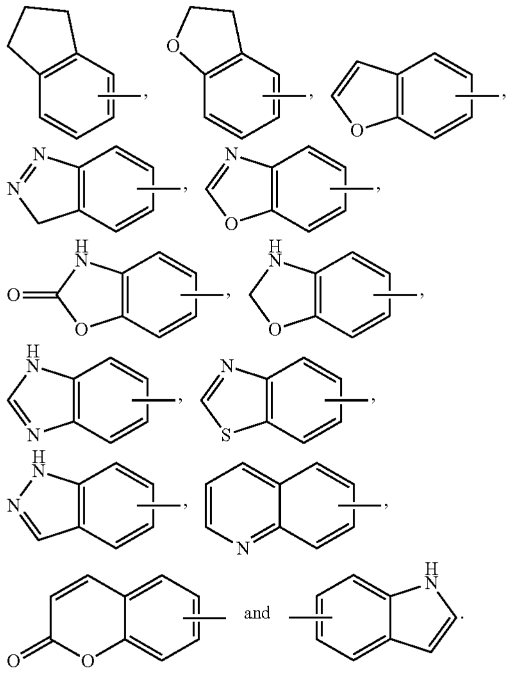

The aryl may be substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like, preferably phenyl.

The term "heteroaryl" refers to a heteroaromatic system containing 1 to 4 heteroatoms and 5 to 14 ring atoms, wherein the heteroatoms are selected from the group consisting of oxygen, sulfur and nitrogen. Heteroaryl is preferably 6- to 12-membered, more preferably 5- or 6-membered. For example, Non-limiting examples of heteroaryl include: imidazolyl, furyl, thienyl, thiazolyl, pyrazolyl, oxazolyl, pyrrolyl, tetrazolyl, pyridyl, pyrimidinyl, thiadiazole, pyrazine,

, 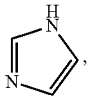, 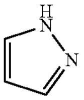

and the like.

The heteroaryl ring may be fused to an aryl, heterocyclyl or cycloalkyl ring, wherein the ring linked to the parent structure is the heteroaryl ring; its non-limiting examples include:

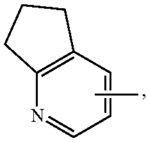, 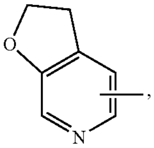, 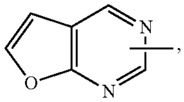,

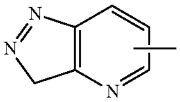, 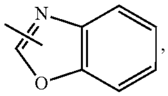,

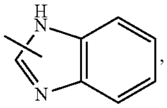, 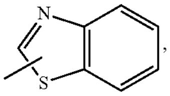,

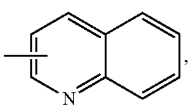, and 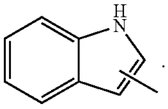.

The heteroaryl may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

The term "alkoxy" refers to —O-(alkyl) and —O-(unsubstituted cycloalkyl), wherein the alkyl is as defined above. Non-limiting examples of alkoxy include: methoxy, ethoxy, propoxy, butoxy, cyclopropyloxy, cyclobutoxy, cyclopentyloxy and cyclohexyloxy. The alkoxy may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-7}$ cycloalkyl, 3-12 membered heterocyclyl, and the like.

The term "hydroxy" refers to the —OH group.

The term "halogen" refers to fluorine, chlorine, bromine, or iodine.

The term "amino" refers to $—NH_2$.

The term "cyano" refers to —CN.

The term "nitro" refers to $—NO_2$.

The term "oxo" refers to the =O substituent.

"Optional" or "optionally" means that the event or circumstance subsequently described may, but does not necessarily, occur, and that the description includes instances where the event or circumstance occurs or does not occur. For example, "a heterocyclyl group optionally substituted with alkyl" means that the alkyl may be, but does not necessarily, present, and that the description includes instances where the heterocyclyl group is or is not substituted with the alkyl.

"Substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue effort. For example, it may be unstable when an amino or hydroxy group having free hydrogen is bound to a carbon atom having an unsaturated (e.g., olefinic) bond.

"Pharmaceutical composition" refers to a mixture containing one or more of the compounds described herein or a physiologically and pharmaceutically acceptable salt or prodrug thereof, and other chemical components, for example physiologically and pharmaceutically acceptable carriers and excipients. The pharmaceutical composition is intended to promote the administration to an organism, so as to facilitate the absorption of the active ingredient, thereby exerting biological activity.

DETAILED DESCRIPTION

The following examples further illustrate the present disclosure, but the present disclosure is not limited thereto.

Experimental procedures without conditions specified in the examples of the present disclosure were generally conducted according to conventional conditions, or according to conditions recommended by the manufacturers of the starting materials or commercial products. Reagents without specific origins indicated are commercially available conventional reagents.

The structures of the compounds were determined by nuclear magnetic resonance (NMR) spectroscopy and/or mass spectrometry (MS). NMR shifts (δ) were given in $10^{-6}$ (ppm). NMR analysis was performed on a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as solvents and tetramethylsilane (TMS) as an internal standard.

MS analysis was performed on a Shimadzu 2010 Mass Spectrometer or Agilent 6110A MSD Mass Spectrometer.

HPLC analysis was performed on Shimadzu LC-20A systems, Shimadzu LC-2010HT series, or Agilent 1200 LC high-performance liquid chromatograph (Ultimate XB-C18 3.0×150 mm chromatography column or Xtimate C18 2.1×30 mm chromatography column).

Chiral HPLC analysis used Chiralpak IC-3 100×4.6 mm I.D., 3 μm, Chiralpak AD-3 150×4.6 mm I.D., 3 μm, Chiralpak AD-3 50×4.6 mm I.D., 3 μm, Chiralpak AS-3 150×4.6 mm I.D., 3 μm, Chiralpak AS-3 100×4.6 mm I.D., 3 μm, ChiralCel OD-3 150×4.6 mm I.D., 3 μm, Chiralcel OD-3 100×4.6 mm I.D., 3 μm, ChiralCel OJ-H 150×4.6 mm I.D., 5 μm, and Chiralcel OJ-3 150×4.6 mm I.D., 3 μm chromatography columns.

Yantai Huanghai HSGF254 or Qingdao GF254 silica gel plates, 0.15-0.2 mm layer thickness, were adopted for thin-layer chromatography (TLC) analysis and 0.4-0.5 mm layer thickness for TLC separation and purification.

Yantai Huanghai silica gel of 100-200 mesh, 200-300 mesh or 300-400 mesh was generally used as a carrier in column chromatography.

Preparative chiral chromatography used DAICEL CHIRALPAK IC (250 mm×30 mm, 10 μm) or Phenomenex-Amylose-1 (250 mm×30 mm, 5 μm).

The CombiFlash preparative flash chromatograph used was CombiFlash Rf150 (TELEDYNE ISCO).

The mean inhibition of kinase and the $IC_{50}$ value were determined on a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions can all be performed in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Pressurized hydrogenation reactions were performed using a Parr 3916EKX hydrogenator and a Qinglan QL-500 hydrogenator, or an HC2-SS hydrogenator.

Hydrogenation reactions generally involved 3 cycles of vacuumization and hydrogen purging.

Microwave reactions were performed on a CEM Discover-S 908860 microwave reactor.

In the examples, a solution refers to an aqueous solution unless otherwise specified.

In the examples, the reaction temperature refers to room temperature, i.e., 20° C. to 30° C., unless otherwise specified.

The reaction processes in the examples were monitored by thin-layer chromatography (TLC).

For the developing solvent for reactions, the eluent system for column chromatography purification and the developing solvent system for thin-layer chromatography, the volume ratio of the solvents was adjusted according to the polarity of the compound, or by adding a small amount of basic or acidic reagents such as triethylamine and acetic acid.

Example 1

(3S,4R)-4-((5-Fluoro-4-(8-fluoro-2,3-dimethyl-3,4-dihydro-5-oxa-1,2a-diazaacenaphthylen-6-yl)pyrimidin-2-yl)amino)tetrahydro-2H-pyran-3-ol isomer 1

(3S,4R)-4-((5-fluoro-4-(8-fluoro-2,3-dimethyl-3,4-dihydro-5-oxa-1,2a-diazaacenaphthylen-6-yl)pyrimidin-2-yl)amino)tetrahydro-2H-pyran-3-ol isomer 2

Isomer 1

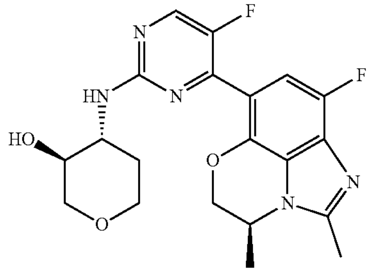

-continued

Isomer 2

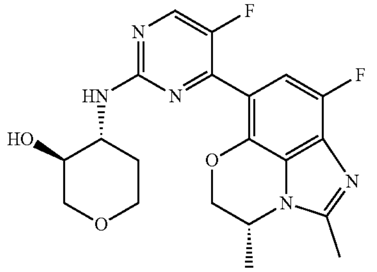

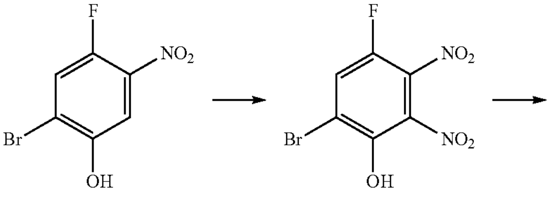

1a 1b

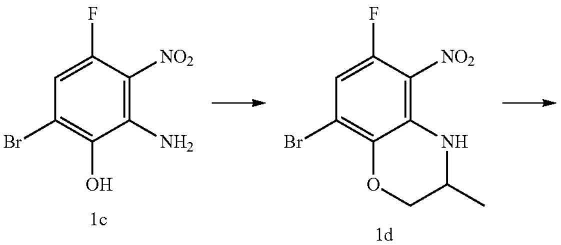

1c 1d

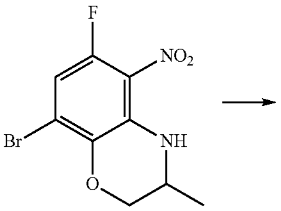

1e

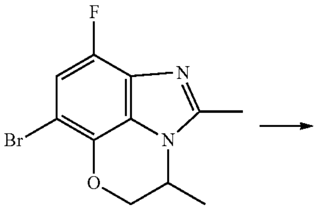

1f

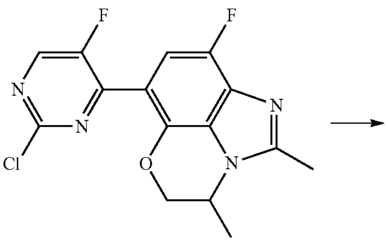

1g

-continued

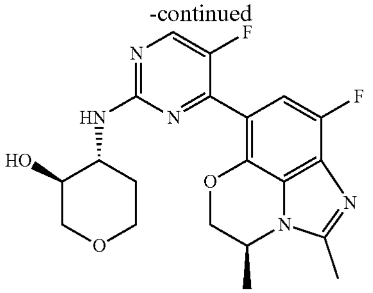

+

Isomer 1

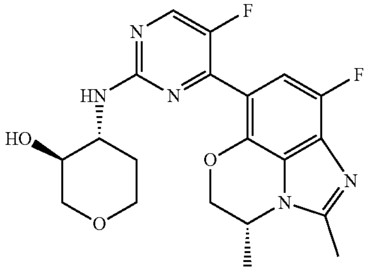

Isomer 2

6-Bromo-4-fluoro-2,3-dinitrophenol 1b

Compound 1a (3.5 g, 14.8 mmol) was dissolved in 16 mL of dichloromethane. A solution of nitric acid in dichloromethane (2 mol/L, 16 mL) was added. The reaction was carried out at room temperature for 20 min. The reaction mixture was poured into 50 mL of ice water. The organic phase was separated, and the aqueous phase was extracted with dichloromethane (50 mL×2). The organic phases were combined, dried over anhydrous sodium sulfate and filtered. The filtrate was collected and concentrated under reduced pressure to give the title compound 1b (3.8 g, yield: 91%).

MS (ESI) m/z 279.0, 281.0 $[M-H]^-$

Step 2

2-Amino-6-bromo-4-fluoro-3-nitrophenol 1c

Compound 1b (3.8 g, 13.5 mmol) was dissolved in 60 mL of methanol. 25 mL of concentrated hydrochloric acid was added, and stannous chloride dihydrate (9.2 g, 40.6 mmol) was added portionwise. The reaction was carried out at room temperature for 20 min. The reaction mixture was concentrated, and 100 mL of saturated sodium bicarbonate solution was added. The mixture was extracted with ethyl acetate (100 mL×3). The organic phases were combined, dried over anhydrous sodium sulfate and filtered. The filtrate was collected and concentrated under reduced pressure. The residue was purified by column chromatography on silica gel using petroleum ether and ethyl acetate as eluents to give the title compound 1c (2.0 g, yield: 59%).

MS (ESI) m/z 249.1, 251.1 $[M-H]^-$

Step 3

8-Bromo-6-fluoro-3-methyl-5-nitro-3,4-dihydro-2H-benzo[b][1,4]oxazine 1d

Compound 1c (200 mg, 0.8 mmol) was dissolved in 4 mL of acetone, and the solution was cooled to 0° C. Potassium carbonate (121 mg, 0.9 mmol) and bromoacetone (120 mg, 0.9 mmol) were added at 0° C. The reaction was carried out at room temperature for 2 h. 20 mL of water was added, and the mixture was extracted with ethyl acetate (20 mL×3). The organic phases were combined, dried over anhydrous sodium sulfate and filtered. The filtrate was collected and concentrated under reduced pressure. The residue was dissolved in 5 mL of tetrahydrofuran. 0.5 mL of trifluoroacetic acid was added, and sodium cyanoborohydride (75 mg, 1.2 mmol) was added portionwise. The reaction was carried out at room temperature for 2 h. The reaction mixture was poured into 20 mL of saturated sodium bicarbonate solution. The mixture was extracted with ethyl acetate (20 mL×3). The organic phases were combined, dried over anhydrous sodium sulfate and filtered. The filtrate was collected and concentrated under reduced pressure. The residue was purified by column chromatography on silica gel using petroleum ether and ethyl acetate as eluents to give the title compound 1d (160 mg, yield: 69%).

MS (ESI) m/z 291.2, 293.2 $[M+H]^+$

Step 4

8-Bromo-6-fluoro-3-methyl-3,4-dihydro-2H-benzo[b][1,4]oxazin-5-amine 1e

Compound 1d (160 mg, 0.5 mmol) was dissolved in 4 mL of methanol. 2 mL of concentrated hydrochloric acid was added, and stannous chloride dihydrate (496 mg, 2.2 mmol) was added portionwise. The reaction was carried out at room temperature for 2 h. The reaction mixture was poured into 20 mL of saturated sodium bicarbonate solution. The mixture was extracted with ethyl acetate (20 mL×3). The organic phases were combined, dried over anhydrous sodium sulfate and filtered. The filtrate was collected and concentrated under reduced pressure. The residue was purified by column chromatography on silica gel using petroleum ether and ethyl acetate as eluents to give the title compound 1e (105 mg, yield: 73%).

MS (ESI) m/z 261.3, 263.3 $[M+H]^+$

Step 5

6-Bromo-8-fluoro-2,3-dimethyl-3,4-dihydro-5-oxa-1,2a-diazaacenaphthylene 1f

Compound 1e (105 mg, 0.4 mmol) was dissolved in 2 mL of concentrated hydrochloric acid. 0.5 mL of acetic acid was added, and the reaction was carried out at 120° C. for 2 h. The reaction mixture was concentrated, and 30 mL of saturated sodium bicarbonate solution was added. The mixture was extracted with ethyl acetate (30 mL×3). The organic phases were combined, dried over anhydrous sodium sulfate and filtered. The filtrate was collected and concentrated under reduced pressure. The residue was purified by C-18 reversed-phase chromatography to give the title compound 1f (17 mg, yield: 15%).

MS (ESI) m/z 241.3, 243.3 $[M+H]^+$

Step 6

6-(2-Chloro-5-fluoropyrimidin-4-yl)-8-fluoro-2,3-dimethyl-3,4-dihydro-5-oxa-1,2a-diazaacenaphthylene 1g Compound 1f (40 mg, 0.14 mmol), bis(pinacolato)diboron (57 mg, 0.22 mmol), potassium acetate (29 mg, 0.29 mmol) and [1,1'-bis(diphenylphosphino)ferrocene]palladium(II) dichloride (21 mg, 0.03 mmol) were sequentially dissolved in 2 mL of 1,4-dioxane in a nitrogen atmosphere. The reaction was carried out at 100° C. for 1 h. The reaction mixture was cooled to room temperature, and 1,3,5,7-tetramethyl-6-phenyl-2,4,8-trioxa-6-phosphaadamantane (8 mg, 0.03 mmol), potassium carbonate (41 mg, 0.29 mmol), 2,4-dichloro-5-fluoropyrimidine (35 mg, 0.21 mmol), tris (dibenzylideneacetone)dipalladium(0) (26 mg, 0.03 mmol) and 0.5 mL of water were added. The reaction was carried out at 80° C. for 1 h. The reaction mixture was cooled to room temperature and filtered. The filtrate was collected and concentrated under reduced pressure. The residue was purified by C-18 reversed-phase chromatography to give the title compound 1g (18 mg, yield: 38%).

MS (ESI) m/z 337.2 $[M+H]^+$

Step 7

(3S,4R)-4-((5-Fluoro-4-(8-fluoro-2,3-dimethyl-3,4-dihydro-5-oxa-1,2a-diazaacenaphthylen-6-yl)pyrimidin-2-yl)amino)tetrahydro-2H-pyran-3-ol isomer 1

(3S,4R)-4-((5-fluoro-4-(8-fluoro-2,3-dimethyl-3,4-dihydro-5-oxa-1,2a-diazaacenaphthylen-6-yl)pyrimidin-2-yl)amino)tetrahydro-2H-pyran-3-ol isomer 2

Compound 1g (18 mg, 0.05 mmol), (3S,4R)-4-aminotetrahydro-2H-pyran-3-ol (7.5 mg, 0.06 mmol), (S)-(−)-2,2"-bis(diphenylphosphino)-1,1"-binaphthyl (6.2 mg, 0.01 mmol) and palladium acetate (2.2 mg, 0.01 mmol) were sequentially dissolved in 2 mL of tetrahydrofuran in a nitrogen atmosphere. Cesium carbonate (41 mg, 0.13 mmol) was added, and the reaction was carried out at 80° C. for 1 h.

The reaction was cooled to room temperature and filtered. The filtrate was collected and concentrated under reduced pressure. The residue was purified by C-18 reversed-phase chromatography to give a crude mixture. The crude product was chirally resolved (column: DAICEL CHIRALPAK AD (250 mm×30 mm, 10 μm); conditions: 45% EtOH (0.1% $NH_3{\cdot}H_2O$) in $CO_2$; flow rate: 80 mL/min) into isomer 1 (3.8 mg, yield: 17%) and isomer 2 (4.4 mg, yield: 20%).

Analysis Method

Column: DAICEL CHIRALPAK AD-3 (150 mm×4.6 mm, 3 μm);

condition: 40% EtOH (0.05% DEA) under a $CO_2$ condition;

flow rate: 2.5 mL/min;

ABPR: 1500 psi;

temperature: 35° C.

The compound with a retention time of 2.903 min was defined as isomer 1; MS (ESI) m/z 418.3 $[M+H]^+$.

The compound with a retention time of 3.997 min was defined as isomer 2; MS (ESI) m/z 418.3 $[M+H]^+$.

Example 2

(3R,4R)-4-((5-Chloro-4-(8-fluoro-2,3-dimethyl-3,4-dihydro-5-oxa-1,2a-diazaacenaphthylen-6-yl)pyrimidin-2-yl)amino)-1-(methylsulfonyl)piperidin-3-ol isomer 1

(3R,4R)-4-((5-Chloro-4-(8-fluoro-2,3-dimethyl-3,4-dihydro-5-oxa-1,2a-diazaacenaphthylen-6-yl)pyrimidin-2-yl)amino)-1-(methylsulfonyl)piperidin-3-ol isomer 2

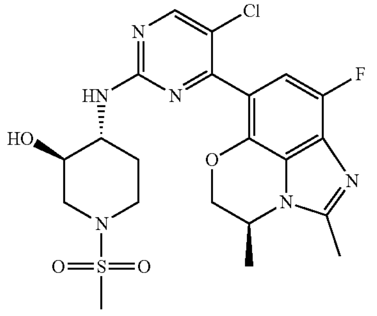

Isomer 1

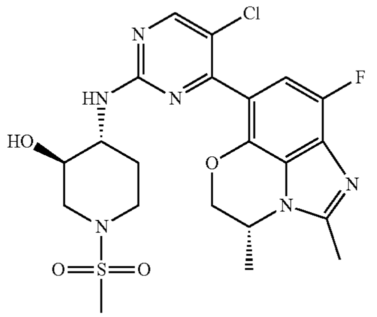

Isomer 2

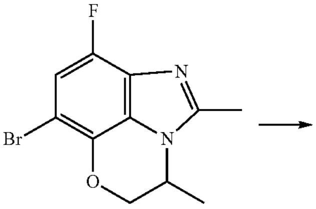

1f

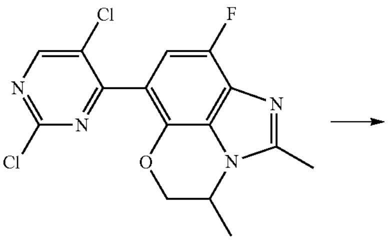

2a

-continued

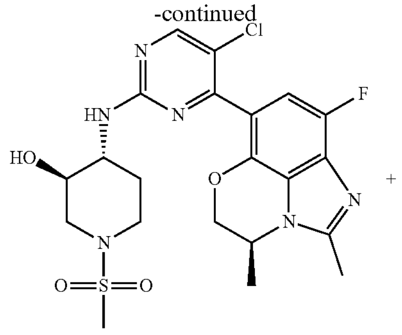

Isomer 1

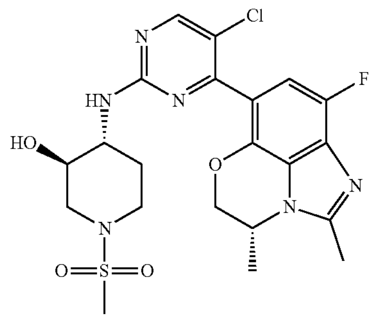

Isomer 2

Step 1

6-(2,5-Dichloropyrimidin-4-yl)-8-fluoro-2,3-dimethyl-3,4-dihydro-5-oxa-1,2a-diazaacenaphthylene 2a Compound 1f (50 mg, 0.18 mmol), bis(pinacolato)diboron (67 mg, 0.26 mmol), potassium acetate (37 mg, 0.38 mmol) and [1,1'-bis(diphenylphosphino)ferrocene]palladium(II) dichloride (26 mg, 0.04 mmol) were sequentially dissolved in 2 mL of 1,4-dioxane in a nitrogen atmosphere. The reaction was carried out at 100° C. for 1 h. The reaction mixture was cooled to room temperature, and 1,3,5,7-tetramethyl-6-phenyl-2,4,8-trioxa-6-phosphaadamantane (10 mg, 0.04 mmol), potassium carbonate (51 mg, 0.37 mmol), 2,4-dichloro-5-fluoropyrimidine (52 mg, 0.28 mmol), tris (dibenzylideneacetone)dipalladium(0) (32 mg, 0.04 mmol) and 0.5 mL of water were added. The reaction was carried out at 80° C. for 1 h. The reaction mixture was cooled to room temperature and filtered. The filtrate was collected and concentrated under reduced pressure. The residue was purified by C-18 reversed-phase chromatography to give the title compound 2a (30 mg, yield: 48%).

MS (ESI) m/z 353.1 [M+H]$^+$

Step 2

(3R,4R)-4-((5-Chloro-4-(8-fluoro-2,3-dimethyl-3,4-dihydro-5-oxa-1,2a-diazaacenaphthylen-6-yl)pyrimidin-2-yl)amino)-1-(methylsulfonyl)piperidin-3-ol isomer 1

(3R,4R)-4-((5-Chloro-4-(8-fluoro-2,3-dimethyl-3,4-dihydro-5-oxa-1,2a-diazaacenaphthylen-6-yl)pyrimidin-2-yl)amino)-1-(methylsulfonyl)piperidin-3-ol isomer 2

Compound 2a (30 mg, 0.08 mmol), (3R,4R)-4-amino-1-(methylsulfonyl)piperidin-3-ol (19.4 mg, 0.10 mmol, prepared using the method disclosed in the patent application "WO 2019/207463 A1"), (S)-(−)-2,2"-bis(diphenylphosphino)-1,1"-binaphthyl (10 mg, 0.02 mmol) and palladium acetate (4.4 mg, 0.02 mmol) were sequentially dissolved in 2 mL of tetrahydrofuran in a nitrogen atmosphere. Cesium carbonate (52 mg, 0.16 mmol) was added, and the reaction was carried out at 80° C. for 1 h. The reaction was cooled to room temperature and filtered. The filtrate was collected and concentrated under reduced pressure. The residue was purified by C-18 reversed-phase chromatography to give a crude mixture. The crude product was chirally resolved (column: DAICEL CHIRALCEL OD-H (250 mm×30 mm, 5 μm); 50% EtOH (0.1% $NH_3{\cdot}H_2O$) in $CO_2$; flow rate: 80 mL/min) into isomer 1 (4.4 mg, yield: 10%) and isomer 2 (3.3 mg, yield: 8%).

Analysis Method

Column: DAICEL CHIRALPAK AD-3 (50 mm×4.6 mm, 3 μm);

mobile phases: A: $CO_2$; B: isopropanol (0.05% DEA); gradient: 5%-40% B within 2 min, maintaining 40% B for 1.2 min, then 5% B for 0.8 min;

flow rate: 4 mL/min;

ABPR: 1500 psi;

temperature: 35° C.

The compound with a retention time of 2.094 min was defined as isomer 1;

MS (ESI) m/z 511.3 [M+H]$^+$ $^1$H NMR (400 MHz, DMSO-d6) δ=8.38 (s, 1H), 7.48 (br s, 1H), 6.91 (br d, J=11.0 Hz, 1H), 5.21 (br s, 1H), 4.86 (br d, J=6.5 Hz, 1H), 4.52-4.44 (m, 1H), 4.24 (br d, J=10.8 Hz, 1H), 3.77 (br s, 1H), 3.64-3.55 (m, 2H), 3.48 (br d, J=13.6 Hz, 1H), 2.89 (s, 3H), 2.69-2.63 (m, 1H), 2.60 (s, 3H), 1.39 (d, J=6.8 Hz, 3H), 1.24 (br s, 2H), 1.18-1.04 (m, 1H).

The compound with a retention time of 2.499 min was defined as isomer 2;

MS (ESI) m/z 511.3 [M+H]$^+$ $^1$H NMR (400 MHz, DMSO-d6) δ=8.38 (s, 1H), 7.47 (br s, 1H), 6.91 (br d, J=11.5 Hz, 1H), 5.21 (br d, J=4.0 Hz, 1H), 4.86 (br d, J=6.5 Hz, 1H), 4.48 (dd, J=1.8, 11.5 Hz, 1H), 4.36 (t, J=5.0 Hz, 2H), 4.24 (br d, J=9.5 Hz, 1H), 3.76 (br s, 1H), 3.59 (br d, J=8.0 Hz, 2H), 2.89 (s, 3H), 2.67 (br d, J=9.3 Hz, 1H), 2.60 (s, 3H), 1.58-1.46 (m, 1H), 1.39 (d, J=6.8 Hz, 3H), 1.24 (br s, 1H).

Example 3

(3S,4R)-4-((5-Chloro-4-((S)-8-fluoro-2,3-dimethyl-3,4-dihydro-5-oxa-1,2a-diazaacenaphthylen-6-yl)pyrimidin-2-yl)amino)tetrahydro-2H-pyran-3-ol isomer 1

(3S,4R)-4-((5-Chloro-4-((R)-8-fluoro-2,3-dimethyl-3,4-dihydro-5-oxa-1,2a-diazaacenaphthylen-6-yl)pyrimidin-2-yl)amino)tetrahydro-2H-pyran-3-ol isomer 2

Isomer 1

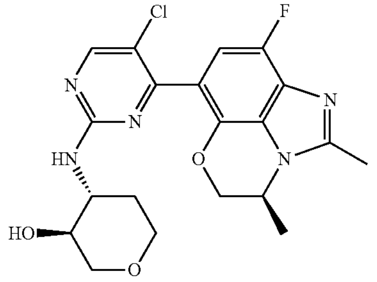

Isomer 2

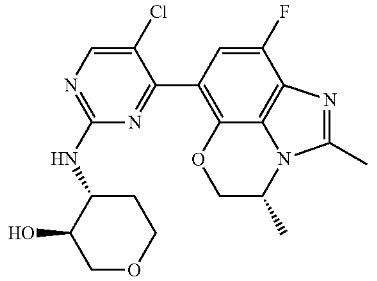

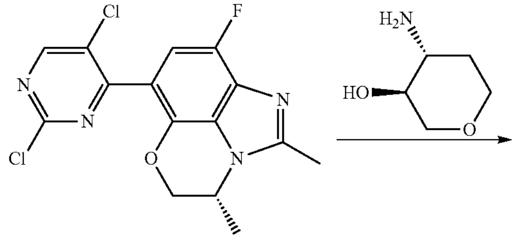

2a

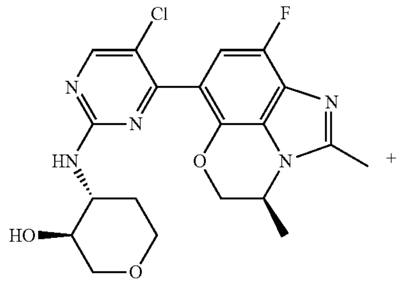

Isomer 1

-continued

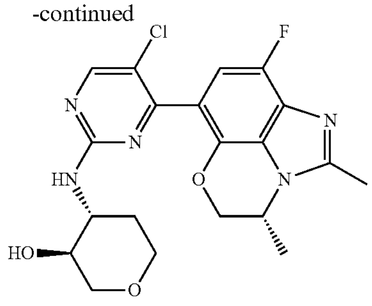

Isomer 2

Compound 2a (55 mg, 0.16 mmol), (3S,4R)-4-aminotetrahydro-2H-pyran-3-ol (18 mg, 0.16 mmol), (S)-(−)-2,2"-bis(diphenylphosphino)-1,1"-binaphthyl (20 mg, 0.03 mmol) and palladium acetate (6.7 mg, 0.03 mmol) were sequentially dissolved in 3 mL of tetrahydrofuran in a nitrogen atmosphere. Cesium carbonate (104 mg, 0.32 mmol) was added, and the reaction was carried out at 85° C. for 3 h. The reaction mixture was cooled to room temperature and filtered. The filtrate was collected and concentrated under reduced pressure. The residue was purified by C-18 reversed-phase chromatography to give a crude mixture. The crude product was chirally resolved [column: DAICEL CHIRALPAK AD (250 mm×30 mm, 10 μm); conditions: 0.1% $NH_3 \cdot H_2O$ IPA, Begin B: 45%; End B: 45%; flow rate (mL/min): 70)] into isomer 1 (6.2 mg, yield: 9.2%) and isomer 2 (7.7 mg, yield: 11%).

Analysis Method

Column: DAICEL CHIRALCEL OD-3 (100 mm×4.6 mm, 3 μm);

mobile phases: A: $CO_2$; B: ethanol (0.05% DEA); gradient: 5%-40% B within 4 min, maintaining 40% B for 2.5 min, then 5% B for 1.5 min;

flow rate: 2.8 mL/min;

ABPR: 1500 psi;

temperature: 35° C.

The compound with a retention time of 3.518 min was defined as isomer 1;

MS (ESI) m/z 434.3 $[M+H]^+$ $^1H$ NMR (400 MHz, DMSO-d6) δ=8.37 (s, 1H), 7.45 (br s, 1H), 6.90 (d, J=11.5 Hz, 1H), 4.93 (d, J=5.3 Hz, 1H), 4.86 (br d, J=6.8 Hz, 1H), 4.48 (dd, J=1.6, 11.7 Hz, 1H), 4.24 (br d, J=9.3 Hz, 1H), 3.84-3.74 (m, 3H), 3.53-3.40 (m, 2H), 3.03 (br t, J=10.2 Hz, 1H), 2.60 (s, 3H), 2.01-1.90 (m, 1H), 1.54-1.44 (m, 1H), 1.38 (d, J=6.5 Hz, 3H).

The compound with a retention time of 4.165 min was defined as isomer 2;

MS (ESI) m/z 434.3 $[M+H]^+$ $^1H$ NMR (400 MHz, DMSO-d6) δ=8.37 (s, 1H), 7.46 (br s, 1H), 6.91 (br d, J=11.5 Hz, 1H), 4.93 (d, J=5.3 Hz, 1H), 4.86 (br d, J=6.5 Hz, 1H), 4.47 (br d, J=10.5 Hz, 1H), 4.23 (br d, J=9.8 Hz, 1H), 3.86-3.74 (m, 3H), 3.54-3.44 (m, 1H), 3.32-3.27 (m, 1H), 3.03 (br t, J=10.3 Hz, 1H), 2.60 (s, 3H), 1.95 (br d, J=13.1 Hz, 1H), 1.54-1.43 (m, 1H), 1.38 (d, J=6.5 Hz, 3H).

Example 4

(3S,4R)-4-((5-Chloro-4-((S)-8-fluoro-2-(2-hydroxy-propan-2-yl)-3-methyl-3,4-dihydro-5-oxa-1,2a-diaz-aacenaphthylen-6-yl)pyrimidin-2-yl)amino)tetra-hydro-2H-pyran-3-ol isomer 1

(3S,4R)-4-((5-Chloro-4-((R)-8-fluoro-2-(2-hydroxy-propan-2-yl)-3-methyl-3,4-dihydro-5-oxa-1,2a-diaz-aacenaphthylen-6-yl)pyrimidin-2-yl)amino)tetra-hydro-2H-pyran-3-ol isomer 2

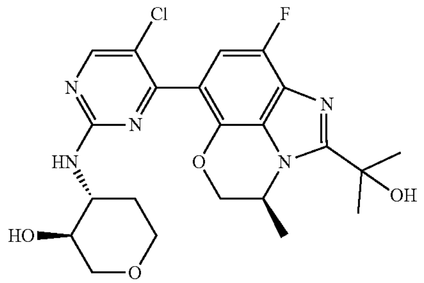

Isomer 1

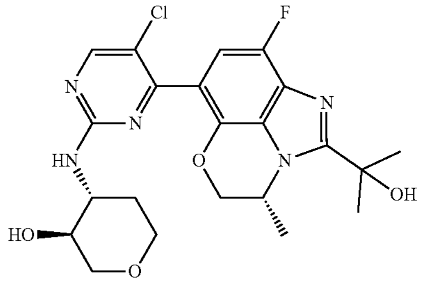

Isomer 2

6-Bromo-8-fluoro-3-methyl-3,4-dihydro-5-oxa-1,2a-diazaacenaphthylene-2-carbaldehyde 4a Compound 1f (2.0 g, 7 mmol) and selenium dioxide (3.1 g, 28 mmol) were sequentially added to 30 mL of 1,4-dioxane in a nitrogen atmosphere. The reaction was carried out at 95° C. for 8 h. The reaction mixture was cooled to room temperature and filtered. The filtrate was collected and concentrated under reduced pressure. The residue was purified by C-18 reversed-phase chromatography to give the title compound 4a (930 mg, yield: 44%).

MS (ESI) m/z 299.1, 301.1 $[M+H]^+$

Step 2

1-(6-Bromo-8-fluoro-3-methyl-3,4-dihydro-5-oxa-1,2a-diazaacenaphthylen-2-yl)ethan-1-ol 4b Compound 4a (930 mg, 3.1 mmol) was dissolved in 20 mL of tetrahydrofuran in a nitrogen atmosphere. The temperature was reduced to −20° C. A solution of methylmagnesium bromide in tetrahydrofuran (3 mol/L, 1.5 mL, 4.5 mmol) was added dropwise, and the reaction was carried out at −20° C. for 4 h. The reaction was quenched with 5 mL of water. The reaction mixture was concentrated under reduced pressure. The residue was purified by C-18 reversed-phase chromatography to give the title compound 4b (830 mg, yield: 85%).

MS (ESI) m/z 315.2, 317.2 $[M+H]^+$

Step 3

1-(6-Bromo-8-fluoro-3-methyl-3,4-dihydro-5-oxa-1,2a-diazaacenaphthylen-2-yl)ethan-1-one 4c Compound 4b (600 mg, 1.9 mmol) was dissolved in 20 mL of tetrahydrofuran at room temperature, and Dess-Martin periodinane (2.0 g, 4.8 mmol) was added. The mixture was heated to 80° C. and was allowed to react for 2 h. The reaction mixture was cooled to room temperature and filtered. The filtrate was collected and concentrated under reduced pressure. The residue was purified by C-18 reversed-phase chromatography to give the title compound 4c (350 mg, yield: 59%).

MS (ESI) m/z 313.1, 315.1 $[M+H]^+$

Step 4

2-(6-Bromo-8-fluoro-3-methyl-3,4-dihydro-5-oxa-1,2a-diazaacenaphthylen-2-yl)propan-2-ol 4d Compound 4c (350 mg, 1.1 mmol) was dissolved in 20 mL of tetrahydrofuran in a nitrogen atmosphere. The temperature was reduced to −20° C. A solution of methylmagnesium bromide in tetrahydrofuran (3 mol/L, 0.7 mL, 2.1 mmol) was added dropwise, and the reaction was carried out at −20° C. for 4 h. The reaction was quenched with 5 mL of water. The reaction mixture was concentrated under reduced pressure. The residue was purified by C-18 reversed-phase chromatography to give the title compound 4d (260 mg, yield: 71%).

MS (ESI) m/z 329.2, 331.2 $[M+H]^+$

Step 5

2-(6-(2,5-Dichloropyrimidin-4-yl)-8-fluoro-3-methyl-3,4-dihydro-5-oxa-1,2a-diazaacenaphthylen-2-yl)propan-2-ol 4e Compound 4d (260 mg, 0.8 mmol), bis(pinacolato)diboron (305 mg, 1.2 mmol), potassium acetate (157 mg, 1.6 mmol) and [1,1'-bis(diphenylphosphino)ferrocene]palladium(II) dichloride (117 mg, 0.2 mmol) were sequentially dissolved in 5 mL of 1,4-dioxane in a nitrogen atmosphere. The reaction was carried out at 100° C. for 2 h. The reaction mixture was cooled to room temperature, and 1,3,5,7-tetramethyl-6-phenyl-2,4,8-trioxa-6-phosphaadamantane (58 mg, 0.2 mmol), potassium carbonate (221 mg, 1.6 mmol), 2,4-dichloro-5-fluoropyrimidine (220 mg, 1.2 mmol), tris(dibenzylideneacetone)dipalladium(0) (183 mg, 0.2 mmol) and 1 mL of water were added. The reaction was carried out at 80° C. for 1 h. The reaction mixture was cooled to room temperature and filtered. The filtrate was collected and concentrated under reduced pressure. The residue was purified by C-18 reversed-phase chromatography to give the title compound 4e (129 mg, yield: 41%).

MS (ESI) m/z 397.3 $[M+H]^+$

Step 6

(3S,4R)-4-((5-Chloro-4-((S)-8-fluoro-2-(2-hydroxy-propan-2-yl)-3-methyl-3,4-dihydro-5-oxa-1,2a-diazaacenaphthylen-6-yl)pyrimidin-2-yl)amino)tetrahydro-2H-pyran-3-ol isomer 1

(3S,4R)-4-((5-Chloro-4-(R)-8-fluoro-2-(2-hydroxy-propan-2-yl)-3-methyl-3,4-dihydro-5-oxa-1,2a-diazaacenaphthylen-6-yl)pyrimidin-2-yl)amino)tetrahydro-2H-pyran-3-ol isomer 2

Compound 4e (124 mg, 0.31 mmol), (3S,4R)-4-amino-tetrahydro-2H-pyran-3-ol (19 mg, 0.16 mmol), (S)-(−)-2,2"-bis(diphenylphosphino)-1,1"-binaphthyl (118 mg, 0.5 mmol) and palladium acetate (14 mg, 0.06 mmol) were sequentially dissolved in 5 mL of tetrahydrofuran in a nitrogen atmosphere. Cesium carbonate (202 mg, 0.62 mmol) was added, and the reaction was carried out at 85° C. for 3 h. The reaction mixture was cooled to room temperature and filtered. The filtrate was collected and concentrated under reduced pressure. The residue was purified by C-18 reversed-phase chromatography to give the crude mixture 4f. The crude product was chirally resolved [column: DAICEL CHIRALPAK AD (250 mm×30 mm, 10 μm); conditions: 0.1% $NH_3 \cdot H_2O$ ETOH, Begin B: 40%; End B: 40%; flow rate (mL/min): 60)] into the title compound isomer 1 (25.2 mg, yield: 17%) and the title compound isomer 2 (22 mg, yield: 15%).

Analysis Method

Column: DAICEL CHIRALCEL AD-3 (100 mm×4.6 mm, 3 μm);

mobile phases: A: $CO_2$; B: ethanol (0.05% DEA); gradient: 5%-40% B within 2 min, maintaining 40% B for 1.2 min, then 5% B for 0.8 min;

flow rate: 4 mL/min;

ABPR: 1500 psi;

temperature: 35° C.

The compound with a retention time of 1.887 min was defined as isomer 2;

MS (ESI) m/z 478.1 [M+H]+

$^1$N NMR (400 MHz, DMSO-d6) δ=8.37 (s, 1H), 7.45 (br s, 1H), 6.92 (d, J=11.3 Hz, 1H), 5.82 (br s, 1H), 5.23 (q, J=6.4 Hz, 1H), 4.93 (d, J=5.3 Hz, 1H), 4.47 (d, J=11.0 Hz, 1H), 4.22 (br d, J=11.3 Hz, 1H), 3.89-3.67 (m, 3H), 3.39-3.25 (m, 2H), 3.03 (br t, J=10.2 Hz, 1H), 1.95 (br d, J=10.5 Hz, 1H), 1.68 (s, 3H), 1.62 (s, 3H), 1.54-1.47 (m, 1H), 1.45 (d, J=6.5 Hz, 3H).

The compound with a retention time of 2.078 min was defined as isomer 1;

MS (ESI) m/z 478.1 $[M+H]^+$ $^1$H NMR (400 MHz, DMSO-d6) δ=8.37 (s, 1H), 7.45 (br s, 1H), 6.92 (d, J=11.5 Hz, 1H), 5.82 (s, 1H), 5.29-5.19 (m, 1H), 4.93 (d, J=5.5 Hz, 1H), 4.47 (d, J=11.3 Hz, 1H), 4.21 (br d, J=10.3 Hz, 1H), 3.85-3.75 (m, 3H), 3.53-3.40 (m, 2H), 3.03 (br t, J=10.4 Hz, 1H), 1.94 (br s, 1H), 1.67 (s, 3H), 1.62 (s, 3H), 1.53-1.47 (m, 1H), 1.45 (d, J=6.5 Hz, 3H).

Biological Evaluation

The present invention is further described below using test examples, but these examples are not intended to limit the scope of the present invention.

Test Example 1. Assay of Disclosed Compounds for Cyclin-Dependent Kinase Activity 1. Experimental Materials

| Reagent | Manufacturer | Cat. No. |
|---|---|---|
| CDK4/cyclin D1 kinase activity, CDK6/cyclin D3 kinase activity | | |
| CDK4/cyclin D1 | ProQinase | 0142-0143-1 |
| CDK6/cyclin D3 | Carna | 04-107 |
| Peptide FAM-P18 | GL Biochem | P080319-XY114202 |
| Peptide FAM-P8 | GL Biochem | P100804-XZ112396 |
| ATP | Sigma | A7699-1G |
| DMSO | Sigma | 474382 |
| EDTA | Sigma | E5134 |
| Staurosporine | Selleckchem | S142105 |
| Ribociclib | MCE | HY-15777 |
| Compound A | In-house synthesis | Compound A |
| CDK1/cyclin B kinase activity, CDK9/cyclin T1 kinase activity | | |
| ADP-Glo kinase assay | Promega | V9102 |
| CDK1/cyclin B | proqinase | 0134-0135-1 |
| CDK9/cyclin T1 | Wuxi Biortus | BP480/792/691 |
| PHA-793887 | Selleck | S1487 |
| Histone H1 | SignalChem | H10-54N |
| ATP | Promega | V910B |
| DMSO | Sigma | D8418 |

Compound A is Example A94 of WO 2019/207463A1 and was synthesized using the method disclosed in the patent application.

2. Kinase Activity Assays (CDK4/Cyclin D1, CDK6/Cyclin D3)

In vitro CDK kinase activity was tested using a mobility shift assay. In the experiment, the starting concentration of the test compounds for the inhibition of CDK activity was 300 nM. The concentration was 3-fold diluted to a total of 10 concentrations, and each assay was performed in duplicate. The compound staurosporine was used as a standard control.

1× kinase buffer (CDK2) (50 mM HEPES, pH 7.5, 0.0015% Brij-35), 1× kinase buffer (CDK4) (20 mM HEPES, pH 7.5, 0.01% Triton X-100) and stop solution (100 mM HEPES, pH 7.5, 0.015% Brij-35, 0.2% Coating Reagent #3, 50 mM EDTA) were prepared.

A proper amount of kinase was added to 1× kinase buffer to prepare 2.5× enzyme solution; 5× compound dilution (1× kinase buffer, 10% DMSO) corresponding to the test concentration of the compound was prepared; a proper amount of FAM-labeled polypeptide and ATP was added to 1× kinase buffer to prepare 2.5× substrate solution. 5 μL of 5× compound dilution and 10 μL of 2.5× enzyme solution were added to reaction wells of a 384-well reaction plate, and they were well mixed and incubated at room temperature for 10 min; 10 μL of 2.5× substrate solution was added to the 384-well plate, and the plate was centrifuged at 1000 rpm for 1 min; the reaction plate was incubated at 28° C. for 60 min (biochemical incubator model: SPX-100B-Z); 30 μL of stop solution was added to the 384-well reaction plate to stop the reactions, and the plate was centrifuged at 1000 rpm for 1 min; finally, conversion rate readings were taken on Caliper EZ Reader II (excitation wavelength: 400 nm; emission wavelengths: 445 nm and 520 nm).

The $IC_{50}$ values of the compounds were obtained by fitting using XLFit excel add-in version 5.4.0.8. Fitting formula:

$$Y = \text{Bottom} + (\text{Top} - \text{Bottom})/(1 + 10\hat{\ }((\text{Log IC50} - X) \times \text{Hill Slope})).$$

X: the log value of the compound concentration; Y: the percent inhibition of the compound.

3. Kinase Activity Assays (CDK1/Cyclin B, CDK9/Cyclin T1)

The starting concentration for in vitro CDK (CDK2 and CDK9) kinase activity assays was 1 μM. The concentration was 3-fold diluted to a total of 10 concentrations, and each assay was performed in duplicate. The compound PHA-793887 was used as a control compound.

1× kinase reaction buffer (40 mM Tris-HCl, pH 7.4, 20 mM Mg2Cl2, 0.1 mg/mL BSA, 50 μM DTT), 1 volume of 5× kinase reaction buffer and 4 volumes of water were prepared, and DTT (final concentration: 50 μM) was added. 50 nL of diluted compound working solution (final concentration of DMSO was 1%) was transferred to each well of a reaction plate (784075, Greiner) using Echo655. The reaction plate was sealed with a plate sealing film and centrifuged at 1000 g for 1 min. 2× enzyme (0.3 ng/μL CDK2/cyclin E1 or CDK9/cyclin T1) was prepared using 1× kinase reaction buffer. 2.5 μL of the above kinase solution was added to each well. The reaction plate was sealed with a plate sealing film, centrifuged at 1000 g for 1 min and left at room temperature for 10 min. A mixture of 2× kinase substrate and ATP was prepared using 1× kinase reaction buffer. 2× CDK2/CylinE1 kinase substrate was 0.4 mg/mL histone H1 and 30 μM ATP. 2.5 μL of the mixture of 2× histone H1 and ATP was added to the reaction plate. The plate was centrifuged at 1000 g for 30 s, and the reaction was started. After the kinase assay reaction was carried out at room temperature for 120 min, 4 μL of ADP-Glo reagent was added, and the reaction was carried out at room temperature for 40 min. Then 8 μL of kinase assay reagent was added, and the reaction was carried out at room temperature for 40 min. The luminescence signals were read using Envision 2104.

Data analysis is shown below:

a) Percent inhibition:

% inhibition=100−(Signalcmpd−SignalAve_PC)/(SignalAve_VC−SignalAve_PC)×100.

SignalAve_PC: an average value for all positive control wells in the whole plate.

SignalAve_VC: an average value for all negative control wells in the whole plate.

Signalcmpd: an average value for wells corresponding to the test compounds.

b) Compound $IC_{50}$: obtained using GraphPad 8.0 and the following non-linear fitting formula:

$Y$=Bottom+(Top−Bottom)/(1+10^((Log IC50−$X$)×Hill Slope)).

X: the log value of the compound concentration; Y: the percent inhibition of the compounds.

The biochemical inhibitory activity of the compounds of the present disclosure against CDKs (CDK1, CDK4, CDK6 and CDK9) was determined through the above assays. The determined $IC_{50}$ values are shown in Table 1, Table 2 and Table 3.

TABLE 1

| Compound | CDK4/D1 (nM) | CDK6/D3 (nM) |
|---|---|---|
| Staurosporine | 70 | 253 |
| Isomer 1 with a retention time of 2.903 min in Example 1 | 26 | >1000 |
| Isomer 2 with a retention time of 3.997 min in Example 1 | 11 | 301 |

TABLE 1-continued

| Compound | CDK4/D1 (nM) | CDK6/D3 (nM) |
|---|---|---|
| Isomer 1 with a retention time of 2.094 min in Example 2 | 2.5 | 39 |
| Isomer 2 with a retention time of 2.499 min in Example 2 | 1.5 | 9.1 |

TABLE 2

| Compound | CDK4/D1 (nM) | CDK6/D3 (nM) |
|---|---|---|
| Ribociclib | 27 | 77 |
| Isomer 1 with a retention time of 3.518 min in Example 3 | 15 | 64 |
| 4f (racemate) in Example 4 | 15 | 171 |

TABLE 3

| Compound | CDK1/B (nM) | CDK4/D1 (nM) | CDK6/D3 (nM) | CDK9/T1 (nM) |
|---|---|---|---|---|
| Compound A | 325 | 4.8 | 121 | 190 |
| Isomer 2 with a retention time of 1.887 min in Example 4 | >1000 | 14 | 228 | >1000 |
| Isomer 1 with a retention time of 2.078 min in Example 4 | >1000 | 8.2 | 105 | >1000 |

Test Example 2. CYP Inhibition Assays

The metabolic reactions of representative substrates of 5 major human CYP subtypes (CYP1A2, CYP2C9, CYP2C19, CYP2D6, CYP3A4) were evaluated using 150-donor pooled human liver microsomes (purchased from Corning, Cat. No. 452117). The effects of different concentrations of the test compounds on the metabolic reactions of phenacetin (CYP1A2), diclofenac sodium (CYP2C9), S-mephenytoin (CYP2C19), bufuralol hydrochloride (CYP2D6) and midazolam (CYP3A4/5) were determined by liquid chromatography-tandem mass spectrometry (LC/MS/MS).

30 μM phenacetin, 10 μEM diclofenac sodium, 35 μEM S-mephenytoin, 5 μM bufuralol hydrochloride, 3 μM midazolam, 1 mM NADPH, and test compounds (at concentrations of 0.1 μmol/L, 0.3 μmol/L, 1 μmol/L, 3 μmol/L, 10 μmol/L, and 30 μmol/L, respectively) or positive compound or blank control were incubated with 200 μL of a reaction system of pooled human liver microsomes (0.2 mg/mL) (100 mmol/L phosphate buffer, pH 7.4, containing 0.3% by volume of DMSO, 0.6% by volume of acetonitrile, and 0.1% by volume of methanol) at 37° C. for 5 min. Then, 200 μL of acetonitrile containing 3% formic acid and 40 nM internal standard verapamil was added, and the mixture was centrifuged at 4000 rpm for 50 min. The mixture was cooled on ice for 20 min and centrifuged at 4000 rpm for 20 min to precipitate the protein. 200 μL of the supernatant was taken for LC/MS/MS analysis.

The peak area was calculated from the chromatogram. The residual activity rate (%) was calculated by the following formula:

peak area rate=peak area of metabolite/peak area of internal standard residual activity rate (%)=peak area proportion of the test compound group/peak area proportion of the blank group The half maximal inhibitory concentrations ($IC_{50}$) against CYP were calculated by Excel XLfit 5.3.1.3.

The determined half maximal inhibitory concentrations ($IC_{50}$) values against CYP are shown in Table 4 below.

TABLE 4

Half maximal inhibitory concentrations ($IC_{50}$) of the compounds of the present disclosure against CYP

| | Examples No. | | | | |
|---|---|---|---|---|---|
| | CYP 1A2 (μM) | CYP 2C9 (μM) | CYP 2C19 (μM) | CYP 2D6 (μM) | CYP 3A4 (μM) |
| Compound A | >30 | 22 | >30 | >30 | 16 |
| Isomer 2 with a retention time of 1.887 min in Example 4 | >30 | >30 | >30 | >30 | >30 |
| Isomer 1 with a retention time of 2.078 min in Example 4 | >30 | >30 | >30 | >30 | >30 |

Test Example 3. Solubility Testing

The thermodynamic solubility of the compounds was determined in a pH 7.4 phosphate buffer. Both the sample supernatant and the standard of known concentration were tested by LC/MS/MS.

1. Materials and Reagents

Compound A (compound A is Example A94 of WO 2019207463A and was synthesized using the method disclosed in the patent application).

$NaH_2PO_4 \cdot 2H_2O$ (analytical reagent), $NaH_2PO_4$ (analytical reagent), and NaOH (analytical reagent).

1.5 mL flat-bottomed glass tubes (BioTech Solutions); molded polytetrafluoroethylene caps (BioTech Solutions), polytetrafluoroethylene-coated stirring bars (BioTech Solutions), Eppendorf ThermoMixer, and 96-well deep-well plates.

2. Preparation of a 0.01 M, pH 7.4 Sodium Phosphate Buffer 15.6 g of $NaH_2PO_4 \cdot 2H_2O$ was weighed out, placed into a 1 L glass flask and dissolved in 1 L of deionized water. The pH of the solution was approximately 4.7, and then the pH was adjusted to 7.4 with 10 M NaOH.

3. Solubility Determination 1 mg of each compound powder was accurately weighed out and placed in a glass tube.

The pH 7.4 sodium phosphate buffer was added to the glass tube in an amount of 1 mL per mg. A stirring bar was added to each glass tube, and a cap was put on. The sample plate containing the glass tubes was placed into Eppendorf ThermoMixer and incubated at 25° C. at 1100 rpm for 24 h. After the incubation, the caps were removed, and the stirring bars were removed using a magnet. The behavior in each glass tube was recorded. The plate was centrifuged at 25° C. at 4000 rpm for 30 min. 750 μL of the supernatant was collected using a pipette. The tip was washed with acetonitrile for 5 s and then with purified water for 5 s. Then the first 50 μL was discarded as waste, and the remaining 700 μL was added to a 96-well sample plate containing glass tubes. The plate was then centrifuged for 30 min (25° C., 4000 rpm). 10 μL of the sample of the second centrifugation was pipetted into 990 μL of a mixture of acetonitrile and water (1:1) containing an internal standard (100× sample). 10 μL of the dilution was pipetted into 990 μL of a mixture of acetonitrile and water (1:1) containing an internal standard (10,000× sample). The sample dilution factor may vary depending on the solubility level and the LC/MS signal response.

TABLE 5

The recorded behavior and dilution factors

| Record | Behavior of samples in phosphate buffer after 24 h | Dilution factor |
|---|---|---|
| No signal | A completely clear solution | 10000 |
| S | A clear solution with a small amount of solids | 10000 |
| S100 | A clear solution with a large amount of solids | 100 |
| 1 | A solution with a small amount of floating powder | 10000 |
| 2 | A suspension with a small amount of foam | 10000 |
| 3 | A solution with a large amount of floating powder | 100 |
| 4 | A suspension with a large amount of foam | 100 |

4. Preparation of the Standard 1 mg of each compound powder was accurately weighed out and added to a glass tube, and DMSO was added to each glass tube in an amount of 1 mL per mg. A stirring bar was added to each glass tube and a cap was put on. The plate containing glass tubes of the standard was placed into Eppendorf ThermoMixer and incubated at 25° C. at 1,100 rpm for 2 h to fully dissolve the powders. Whether the solids could be completely dissolved was observed, and compounds that could not be completely dissolved in DMSO solution were recorded. 10 μL of 1 mg/mL standard was pipetted into 990 μL of a mixture of acetonitrile and water (1:1) containing an internal standard to give a 10 μg/mL standard. 10 μL of 10 μg/mL standard was pipetted into 990 μL of a mixture of acetonitrile and water (1:1) containing an internal standard to give a 0.1 μg/mL standard. The sample dilution factor may vary depending on the LC/MS signal response. Samples were analyzed by LC/MS/MS. All compounds were tested individually.

5. Calculations

All calculations were performed by Microsoft Excel.

Samples were analyzed by LC/MS/MS and quantified according to the standard of known concentration. The solubility of the test compounds was calculated by the following formula:

$$[\text{sample}] = \text{area ratio sample} \times \text{DF sample} \times [\text{STD}] / \text{area ratio STD}$$

DF: dilution factor.

STD: test compound standard.

TABLE 6

The solubility of the compounds of the present disclosure

| Example No. | Solubility (μM) |
|---|---|
| Compound A | 16 |
| Isomer 2 with a retention time of 1.887 min in Example 4 | 2126 |
| Isomer 1 with a retention time of 2.078 min in Example 4 | 2203 |

Test Example 4. PXR Induction Assays

1. The potential of the test compounds to induce the activity of drug metabolism enzymes by in vitro activating PXR was evaluated. $EC_{50}$ values were obtained by assaying different concentrations of test compounds (30, 10, 3.33, 1.11, 0.370 and 0.123 μM) by in vitro activating PXR. The concentrations of the positive control rifampicin were 20, 5, 1.25, 0.312, 0.0781 and 0.195 μM.

2. Materials and Reagents

1) DPX2 (HepG2 cells were stably transfected with the human PXR gene and the fluorescent reporter gene) cells were purchased from Puracyp (Carlsbad, CA).

2) The test compounds were provided by the sponsor; the control drug (rifampicin) was purchased from Sigma (St. Louis, MO).

3) The CellTiter-Fluor™ cell viability assay kit and the One-Glo fluorescence assay kit were purchased from Promega (Madison, WI); fetal bovine serum (FBS) was purchased from Corning (Manassas, VA); the MTS3 shaker was purchased from IKA Labortechnik (Staufen, Germany); DMEM, penicillin and streptomycin were purchased from local suppliers; hygromycin B and G418 were purchased from Merck (Darmstadt, Germany); the cell culture medium and DPX2 cells were purchased from Puracyp Inc.

3. Procedures 3.1. Plating Preparation 1) 50 mL of FBS was added to 450 mL of cell culture medium.

2) DPX2 cells were cultured in a T-75 culture flask in a 37° C., 5% $CO_2$ incubator with 95% relative humidity. When covering 80-90% of the bottom of the culture flask, the cells were digested.

3) The top layer of the cells cultured in the T-75 culture flask was washed with 8 mL of PBS, and the PBS was pipetted off. The cells were digested with 3 mL of pancreatin at 37° C. for about 5 min or until they were floating in the pancreatin. 10 mL (excessive) of a serum-containing medium was added to neutralize the pancreatin.

4) The cell suspension was transferred to a conical-bottomed centrifuge tube and centrifuged at 120 g for 10 min. The cells were suspended in the plating medium and adjusted to a concentration of $4\times10^5$ cells/mL. 100 μL of diluted cells were added to each well of a 96-well cell culture plate. The culture plate was placed in an incubator and incubated at 37° C. for 24 h before PXR activation assays.

3.2. Addition of Drugs

1) The test compounds and positive compound (rifampicin) were prepared in DMSO and the compounds were diluted with a serum-free medium at 37° C. The final concentrations of the positive control rifampicin were 20, 5, 1.25, 0.312, 0.0781 and 0.195 μM. The final concentrations of the test compounds were 30, 10, 3.33, 1.11, 0.370 and 0.123 μM. The final concentration of DMSO was 0.1%. To 1 mL of pre-incubated medium, 1 μL of DMSO was added as a solvent control.

2) The cell culture plate was removed from the incubator, and the medium was discarded. 100 μL of each of the test compounds and positive compound was added to an appropriate well in duplicate, and the cell plate was placed in an incubator and incubated for 24 h.

3.3. Quantification of PXR Activation

1) After 2 days of drug treatment, quantification of PXR activation could be performed on the culture.

2) The CellTiter-Fluor™ cell viability assay kit and the One-Glo luciferase reagent were equilibrated to room temperature. The GF-AFC (10 μL) substrate was added to assay buffer (10 mL) to form 2× reagent, and the reagent was then diluted to 1× with 10 mL of PBS; the ONE-Glo substrate was added to the ONE-Glo luciferase assay buffer.

3) The cell culture plate was removed from the incubator, and the medium in each well was discarded. The plate was washed twice with PBS. 1× CellTiter-Fluor™ reagent was added to a sterilized reagent reservoir, and 50 μL was transferred to each well using a multi-channel pipette. The plate was incubated at 37° C. for 30 min.

4) The 96-well cell plate was removed from the incubator and analyzed on a microplate reader operating in the fluorescence mode at an excitation wavelength of 400 nm and an emission wavelength of 505 nm to measure the fluorescence value in each well.

5) The ONE-Glo reagent was poured into a reagent reservoir, and then 50 μL was transferred to each well using a multi-channel pipette. The reagent was gently and well mixed, and the mixture was incubated and well mixed at room temperature for 5 min. After the incubation, the luminescence value of each well was read using a luminometer.

4. Calculation of Cell Induction Values 4.1. Cell Viability

The calculation formula for cell viability:

$$\text{Percent cell viability } (\%)=I(\text{sample})/(I(\text{vehicle})\times100$$

I(sample) represents the fluorescence intensity of the sample, and I(vehicle) represents the fluorescence intensity of 0.1% DMSO to the cells.

4.2. Calculation of Cell Induction Values

All data were calculated using Microsoft Excel.

The luciferase activity was expressed in terms of RFU/RLU, where RLU is the mean luminescence intensity value of two replicates of each concentration of each compound, and RFU is the mean fluorescence intensity of two replicates of each concentration of each compound.

The calculation formula for induction fold:

$$\text{Induction fold} = \frac{RLU_{test\ compound}/RFU_{test\ compound}}{RLU_{blank}/RFU_{blank}}$$

TABLE 7

Some of the determined PXR induction values

| Compound | Compound concentration (μM) | Cell viability (%) | Induction fold |
|---|---|---|---|
| Rifampicin | 20.0 | 93.07 | 17.60 |
| | 0.0195 | 103.39 | 1.33 |
| Compound A | 10.0 | 94.32 | 48.51 |
| | 0.123 | 99.67 | 1.04 |
| Isomer 2 with a retention time of 1.887 min in | 10.00 | 108.37 | 1.48 |
| Example 4 | 0.123 | 102.41 | 0.99 |
| Isomer 1 with a retention time of 2.078 min in | 10.00 | 117.18 | 1.43 |
| Example 4 | 0.123 | 99.16 | 0.87 |

The invention claimed is:

1. A compound of formula I or a pharmaceutically acceptable salt thereof,

I

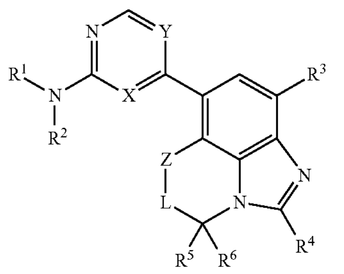

wherein $R^1$ is selected from the group consisting of H, $C_{1-6}$ alkyl, $C_{1-6}$ haloalkyl and $C_{3-8}$ cycloalkyl; the $C_{1-6}$ alkyl, $C_{1-6}$ haloalkyl and $C_{3-8}$ cycloalkyl are each independently and optionally substituted with one or more $R^a$;

$R^2$ is a structure of formula II:

II

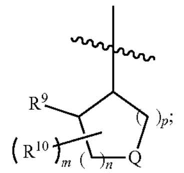

$R^9$ is selected from the group consisting of H, OH and $NH_2$; the $NH_2$ is optionally substituted with 1 or 2 $R^a$ or $R^{a''}$;

each $R^{10}$ is independently selected from the group consisting of OH, halogen, CN, $NH_2$, $C_{1-6}$ alkyl, $C_{1-6}$ alkoxy, $C_{1-6}$ haloalkyl, $C_{1-6}$ haloalkoxy, $C_{3-8}$ cycloalkyl and 3-12 membered heterocycloalkyl; the $C_{1-6}$ alkyl, $C_{1-6}$ alkoxy, $C_{1-6}$ haloalkyl, $C_{3-8}$ cycloalkyl and 3-12 membered heterocycloalkyl are each independently and optionally substituted with one or more $R^b$;

Q is $NR^{11}$ or 0;

or Q is $CR^{12}R^{13}$, wherein $R^{12}$ and $R^{13}$, together with the carbon atom to which they are attached, form a 3-12 membered heterocycloalkyl group containing N or O of $NR^{11}$ as a ring atom; the heterocycloalkyl group is optionally substituted with one or more $R^{10}$;

$R^{11}$ is selected from the group consisting of H, $C_{1-6}$ alkyl, $C_{1-6}$ haloalkyl, $SO_2R^c$, $SO_2NR^dR^e$, $COR^f$, $COOR^f$ and $CONR^gR^h$; the $C_{1-6}$ alkyl and $C_{1-6}$ haloalkyl are each independently and optionally substituted with one or more substituents selected from the group consisting of $R^a$, $R^b$, $SO_2R^c$, $SO_2NR^dR^c$, $COR^f$, COOR and $CONR^gR^h$;

m is 0, 1 or 2;

n is 0, 1, 2, 3 or 4;

p is 1, 2 or 3;

X is N or CH;

Y is N or $CR^7$;

$R^7$ is selected from the group consisting of H, F, Cl, CN, $C_{1-6}$ alkyl and $C_{1-6}$ alkoxy; the $C_{1-6}$ alkyl and $C_{1-6}$ alkoxy are each independently and optionally substituted with one or more $R^a$;

$R^3$ is selected from the group consisting of H, F, Cl, CN, $CH_2F$, $CHF_2$ and $CF_3$;

$R^4$ is selected from the group consisting of H, $C_{1-6}$ alkyl, $C_{1-6}$ alkoxy, $C_{3-8}$ cycloalkyl and 3-12 membered heterocycloalkyl; the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms;

Z is O or $CHR^8$; $R^8$ is selected from the group consisting of hydrogen, deuterium and halogen;

L is $-(CH_2)_q-$; the $-(CH_2)-$ is optionally substituted with one or more substituents selected from the group consisting of deuterium, CN, halogen, $C_{1-6}$ alkyl, $C_{3-8}$ cycloalkyl, $C_{1-6}$ alkoxy and 3-12 membered heterocycloalkyl; the $C_{1-6}$ alkyl, $C_{3-8}$ cycloalkyl, $C_{1-6}$ alkoxy and 3-12 membered heterocycloalkyl are each independently and optionally substituted with one or more $R^b$ or deuterium atoms;

q is 1, 2, 3 or 4;

$R^5$ and $R^6$ are each independently selected from the group consisting of H, deuterium, CN, halogen, $C_{1-6}$ alkyl, $C_{3-8}$ cycloalkyl, $C_{1-6}$ alkoxy and 3-12 membered heterocycloalkyl; the $C_{1-6}$ alkyl, $C_{3-8}$ cycloalkyl, $C_{1-6}$ alkoxy and 3-12 membered heterocycloalkyl are each optionally and independently substituted with one or more $R^b$ or deuterium atoms;

$R^a$ and $R^b$ are each independently selected from the group consisting of H, OH, CN, halogen, $C_{1-6}$ alkyl, $C_{1-6}$ alkoxy, $C_{1-6}$ haloalkyl, $C_{1-6}$ haloalkoxy, $C_{3-8}$ cycloalkyl, 3-12 membered heterocycloalkyl and $NR^{a'}R^{a''}$; the $C_{1-6}$ alkyl, $C_{1-6}$ alkoxy, $C_{1-6}$ haloalkyl, $C_{3-8}$ cycloalkyl and 3-12 membered heterocycloalkyl are each independently and optionally substituted with one or more substituents selected from the group consisting of $NH_2$, $NHCH_3$, $N(CH_3)_2$, halogen, OH, $C_{1-6}$ alkyl, $C_{1-6}$ alkoxy, $C_{1-6}$ haloalkyl, $C_{3-8}$ cycloalkyl and 3-12 membered heterocycloalkyl;

$R^{a'}$ and $R^{a''}$ are each independently selected from the group consisting of H, $C_{1-6}$ alkyl, $C_{1-6}$ haloalkyl, $C_{3-8}$ cycloalkyl and 3-12 membered heterocycloalkyl; the $C_{1-6}$ alkyl, $C_{1-6}$ haloalkyl, $C_{3-8}$ cycloalkyl and 3-12 membered heterocycloalkyl are each independently and optionally substituted with one or more substituents selected from the group consisting of $NH_2$, $NHCH_3$, $N(CH_3)_2$, halogen, OH, $C_{1-6}$ alkyl, $C_{1-6}$ alkoxy, $C_{1-6}$ haloalkyl, $C_{1-6}$ haloalkoxy, $C_{3-8}$ cycloalkyl and 3-12 membered heterocycloalkyl;

or $R^{a'}$ and $R^{a''}$, together with the N atom to which they are attached, form a 3-12 membered heterocycloalkyl group; the 3-12 membered heterocycloalkyl group is optionally substituted with one or more substituents selected from the group consisting of halogen, OH, $C_{1-6}$ alkyl, $C_{1-6}$ alkoxy, $C_{1-6}$ haloalkyl, $C_{1-6}$ haloalkoxy, $C_{3-8}$ cycloalkyl and 3-12 membered heterocycloalkyl;

$R^c$, $R^d$ and $R^e$ are each independently selected from the group consisting of H, $C_{1-6}$ alkyl, $C_{1-6}$ alkoxy, $C_{3-8}$ cycloalkyl and $C_{1-6}$ haloalkyl;

$R^f$ is selected from the group consisting of H, $C_{1-6}$ alkyl, $C_{1-6}$ haloalkyl, $C_{3-8}$ cycloalkyl and 3-12 membered heterocycloalkyl; the $C_{1-6}$ alkyl, $C_{1-6}$ haloalkyl, $C_{3-8}$ cycloalkyl and 3-12 membered heterocycloalkyl are each independently and optionally substituted with one or more substituents selected from the group consisting of $NH_2$, $NHCH_3$, $N(CH_3)_2$, halogen, OH, $C_{1-6}$ alkyl, $C_{1-6}$ alkoxy, $C_{1-6}$ haloalkyl, $C_{3-8}$ cycloalkyl and 3-12 membered heterocycloalkyl;

$R^g$ and $R^h$ are each independently selected from the group consisting of H, $C_{1-6}$ alkyl, $C_{1-6}$ alkoxy, $C_{1-6}$ haloalkyl and $C_{3-8}$ cycloalkyl; the $C_{1-6}$ alkoxy, $C_{1-6}$ haloalkyl and $C_{3-8}$ cycloalkyl are each independently and optionally substituted with one or more $R^a$ or $R^b$.

2. The compound of formula I or the pharmaceutically acceptable salt thereof according to claim 1, wherein $R^1$ is H or $C_{1-6}$ alkyl.

3. The compound of formula I or the pharmaceutically acceptable salt thereof according to claim 1, wherein $R^2$ is selected from the group consisting of

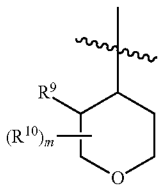
,
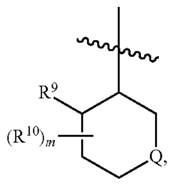
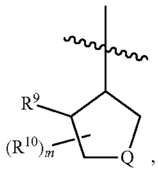
,
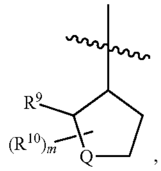
,
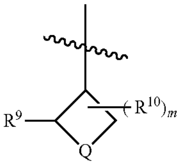
,
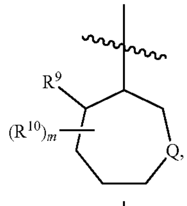
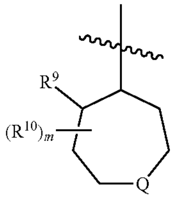
and
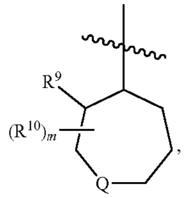

$R^9$, $R^{10}$, m and Q are as defined in claim 1.

4. The compound of formula I or the pharmaceutically acceptable salt thereof according to claim 1, wherein $R^2$ is

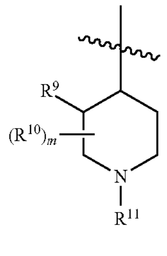
or
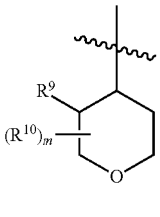
;

$R^9$, $R^{10}$, m and $R^{11}$ are as defined in claim 1.

5. The compound of formula I or the pharmaceutically acceptable salt thereof according to claim 3, wherein $R^9$ is OH or $NH_2$; the $NH_2$ is optionally substituted with 1 or 2 $R^{a'}$ or $R^{a''}$; $R^{a'}$ and $R^{a''}$ are each independently $C_{1-6}$ alkyl.

6. The compound of formula I or the pharmaceutically acceptable salt thereof according to claim 1, wherein X is N.

7. The compound of formula I or the pharmaceutically acceptable salt thereof according to claim 1, wherein Y is $CR^7$; $R^7$ is selected from the group consisting of H, F, Cl and $C_{1-6}$ alkyl.

8. The compound of formula I or the pharmaceutically acceptable salt thereof according to claim 1, wherein $R^3$ is selected from the group consisting of H, F and Cl.

9. The compound of formula I or the pharmaceutically acceptable salt thereof according to claim 1, wherein $R^4$ is selected from the group consisting of H, $C_{1-6}$ alkyl, $C_{1-6}$ alkoxy, $C_{3-8}$ cycloalkyl and 3-12 membered heterocycloalkyl, the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms, and $R^b$ is selected from the group consisting of OH, CN, halogen, $C_{1-6}$ alkyl, $C_{1-6}$ alkoxy, $C_{1-6}$ haloalkyl, $C_{1-6}$ haloalkoxy and $C_{3-8}$ cycloalkyl.

10. The compound of formula I or the pharmaceutically acceptable salt thereof according to claim 1, wherein L is $-(CH_2)_q-$; q is selected from the group consisting of 1 and 2; the $-(CH_2)-$ is optionally substituted with one or more substituents selected from the group consisting of deuterium, CN, halogen, $C_{1-6}$ alkyl, $C_{3-8}$ cycloalkyl, $C_{1-6}$ alkoxy and 3-12 membered heterocycloalkyl.

11. The compound of formula I or the pharmaceutically acceptable salt thereof according to claim 1, wherein $R^5$ and $R^6$ are each independently selected from the group consisting of H, deuterium, CN, halogen, $C_{1-6}$ alkyl and $C_{3-8}$ cycloalkyl.

12. The compound of formula I or the pharmaceutically acceptable salt thereof according to claim 1, being a compound of formula I-3 or a pharmaceutically acceptable salt thereof,

I-3

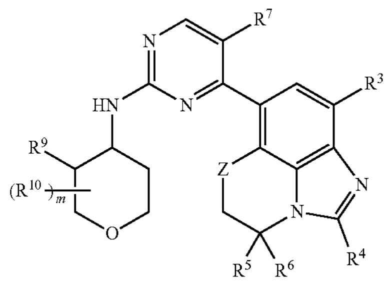

wherein $R^9$ is OH or $NH_2$; the $NH_2$ is optionally substituted with 1 or 2 $R^{a'}$ or $R^{a''}$; $R^{a'}$ and $R^{a''}$ are each independently $C_{1-6}$ alkyl;

$R^{10}$ are each independently selected from the group consisting of OH, halogen, CN, $NH_2$, $C_{1-6}$ alkyl, $C_{1-6}$ alkoxy, $C_{1-6}$ haloalkyl and $C_{1-6}$ haloalkoxy;

m is 0, 1, or 2;

$R^7$ is selected from the group consisting of H, F, Cl and $C_{1-6}$ alkyl;

$R^3$ is selected from the group consisting of H, F and Cl;

$R^4$ is selected from the group consisting of H, $C_{1-6}$ alkyl, $C_{1-6}$ alkoxy, $C_{3-8}$ cycloalkyl and 3-12 membered heterocycloalkyl; the $C_{1-6}$ alkyl, $C_{1-6}$ alkoxy, $C_{3-8}$ cycloalkyl and 3-12 membered heterocycloalkyl are each independently and optionally substituted with one or more $R^b$ or deuterium atoms; $R^b$ is selected from the group consisting of H, OH, CN and halogen;

$R^5$ and $R^6$ are each independently selected from the group consisting of H, deuterium, CN, halogen, $C_{1-6}$ alkyl and $C_{3-8}$ cycloalkyl;

Z is O or $CHR^8$; $R^8$ is selected from the group consisting of hydrogen, deuterium and halogen.

13. The compound of formula I or the pharmaceutically acceptable salt thereof according to claim 12, wherein Z is O.

14. The compound of formula I or the pharmaceutically acceptable salt thereof according to claim 12, wherein Z is $CHR^8$; $R^8$ is selected from the group consisting of hydrogen, deuterium and halogen.

15. The compound of formula I or the pharmaceutically acceptable salt thereof according to claim 13, wherein $R^9$ is OH or $NH_2$; the $NH_2$ is optionally substituted with 1 or 2 $R^a$ or $R^{a''}$; $R^{a'}$ and $R^{a''}$ are each independently $C_{1-6}$ alkyl;

m is 0;

$R^7$ is selected from the group consisting of H, F, Cl and $C_{1-6}$ alkyl;

$R^3$ is selected from the group consisting of H, F and Cl;

$R^4$ is selected from the group consisting of H, $C_{1-6}$ alkyl and $C_{1-6}$ alkoxy; the $C_{1-6}$ alkyl and $C_{1-6}$ alkoxy are each independently and optionally substituted with one or more $R^b$ or deuterium atoms; $R^b$ is selected from the group consisting of H, OH, CN and halogen;

$R^5$ and $R^6$ are each independently selected from the group consisting of H, deuterium, CN, halogen and $C_{1-6}$ alkyl.

16. The compound of formula I or the pharmaceutically acceptable salt thereof according to claim 1, being selected from the group consisting of

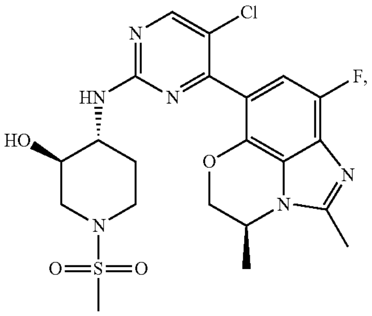

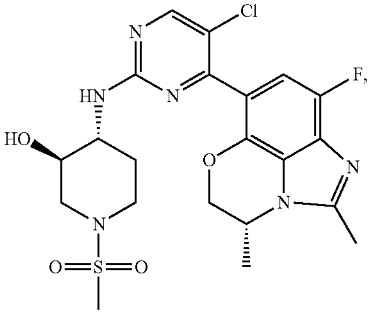

-continued

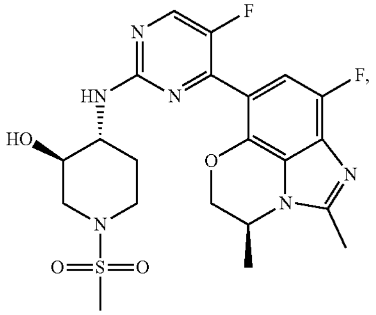

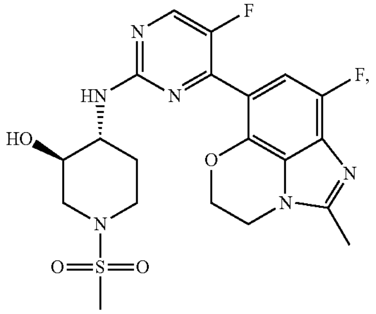

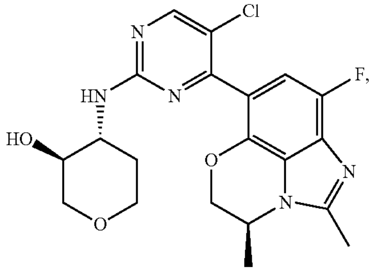

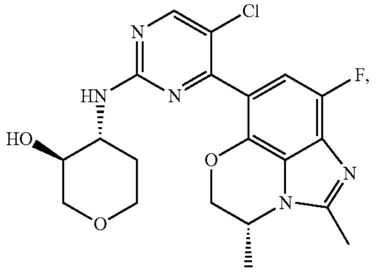

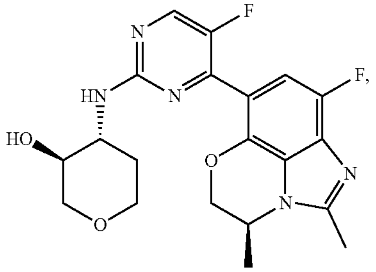

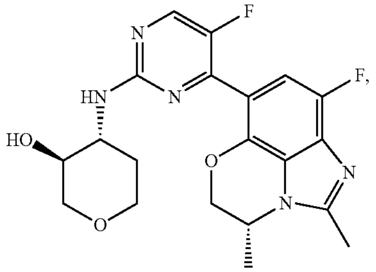

-continued
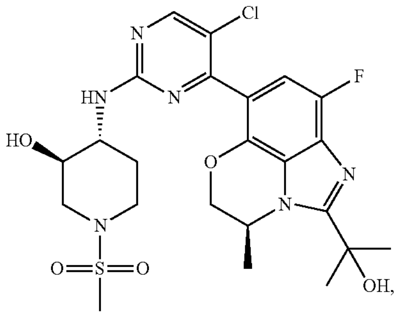,
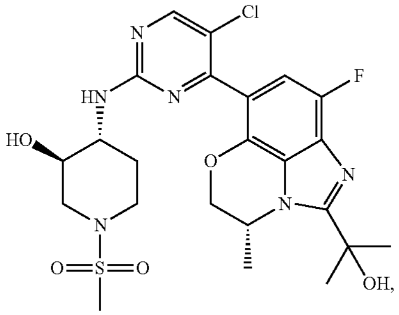,
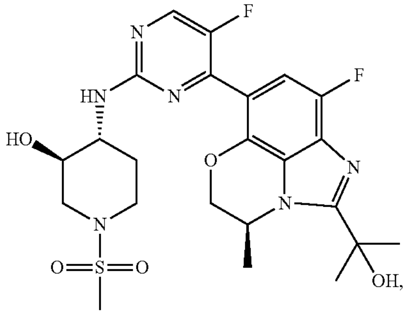,
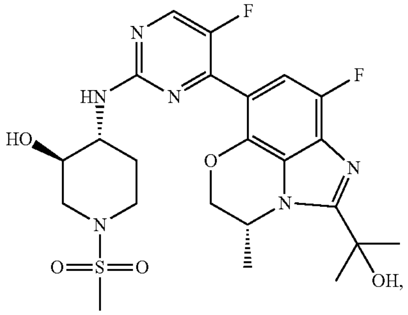,
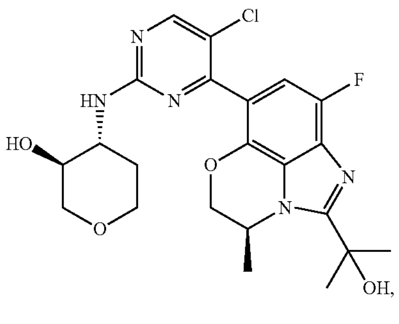,
-continued
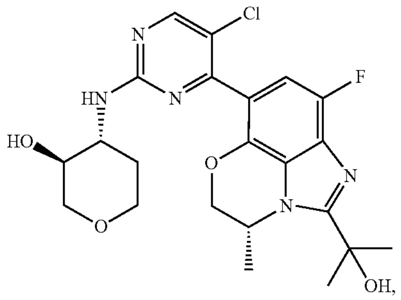,
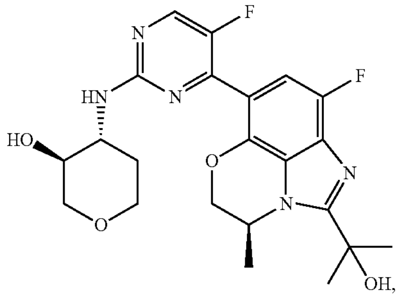,
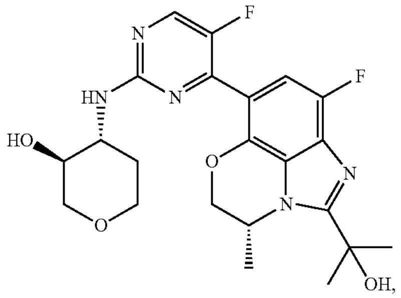,
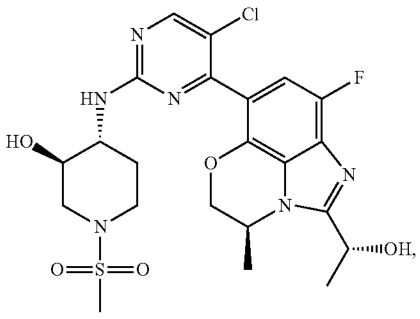,
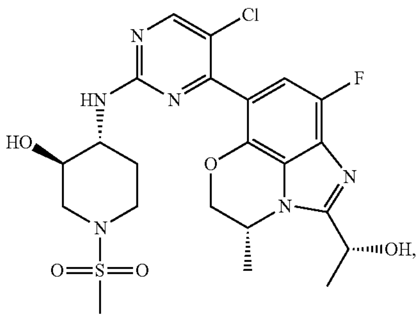, -continued
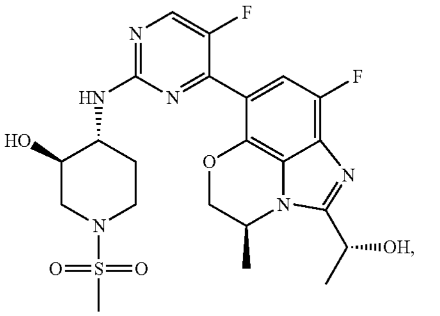
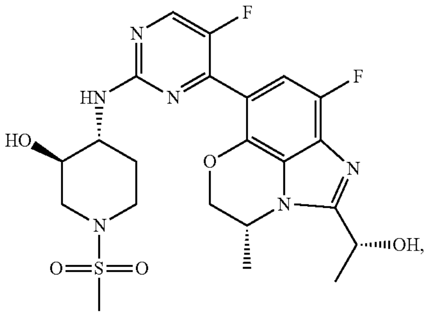
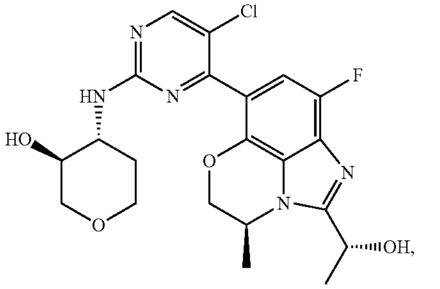
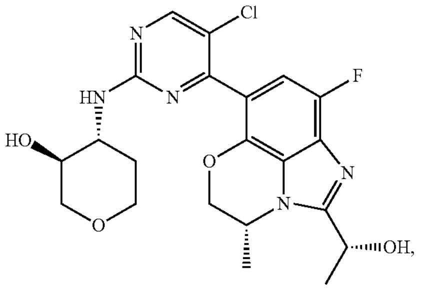
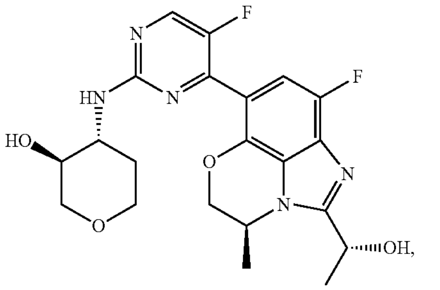
-continued
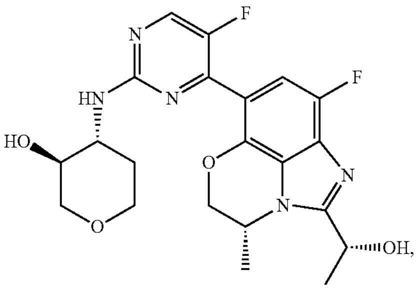
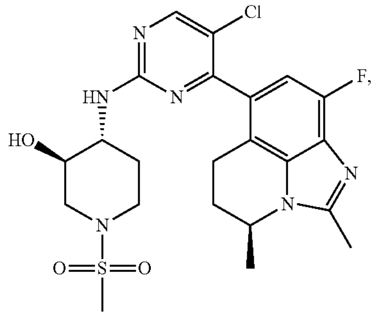
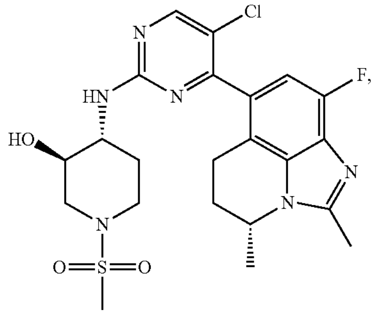
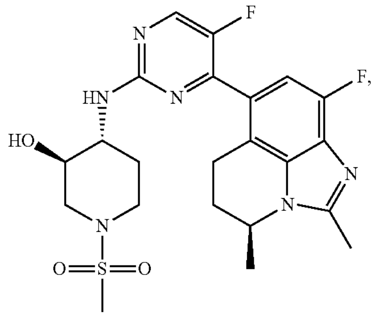
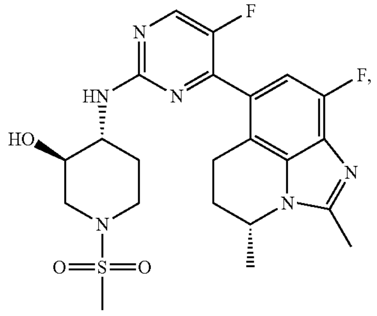

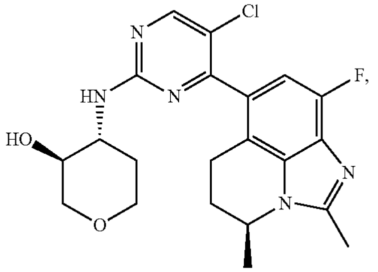
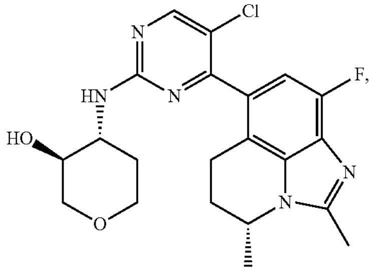
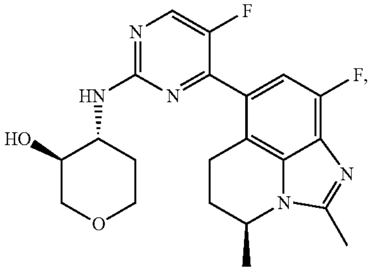
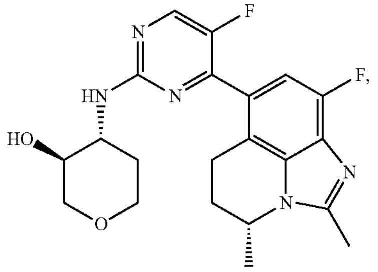
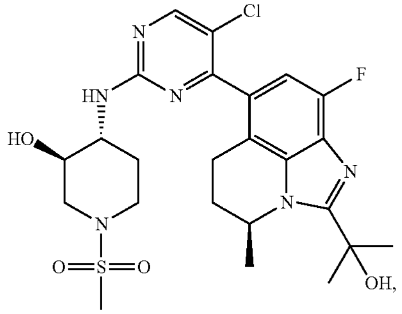
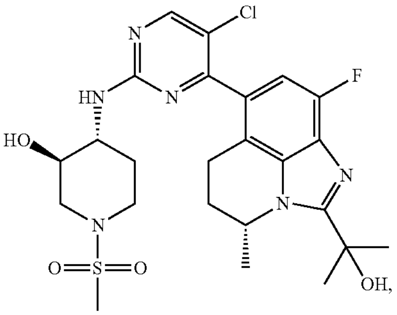
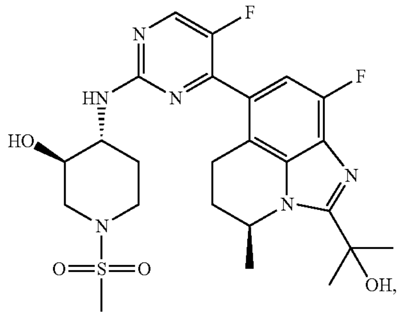
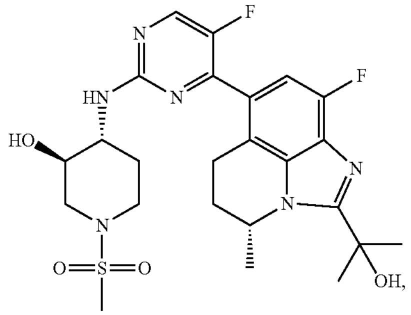
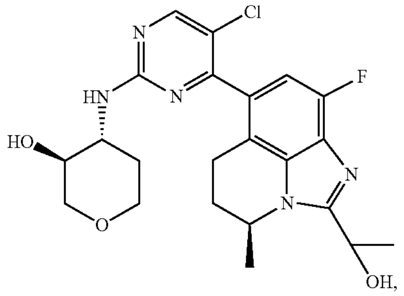
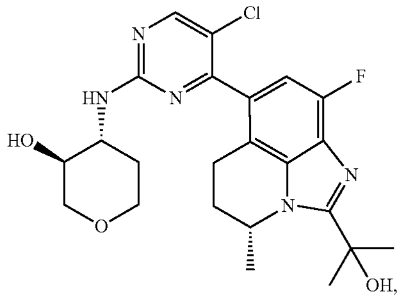
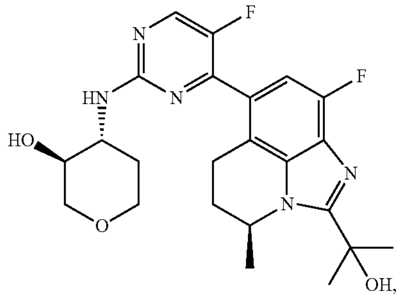

-continued
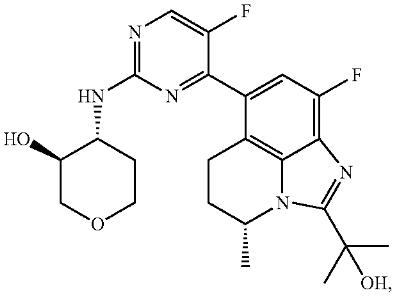
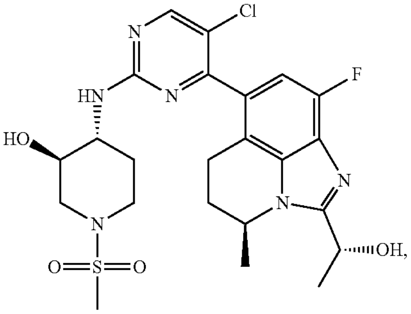
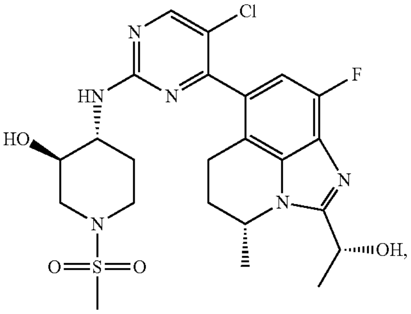
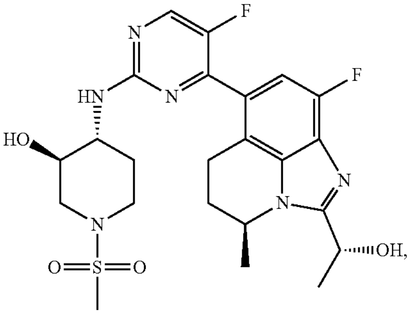
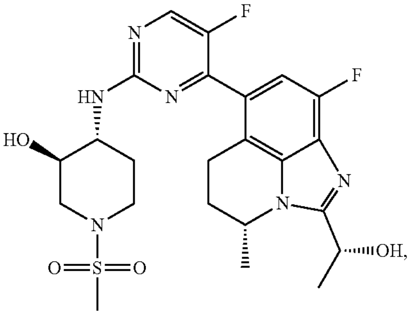
-continued
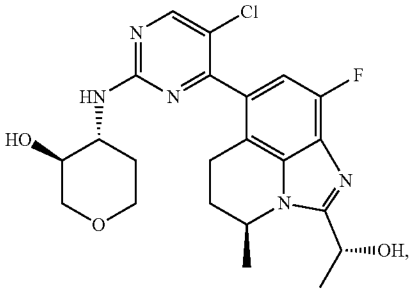
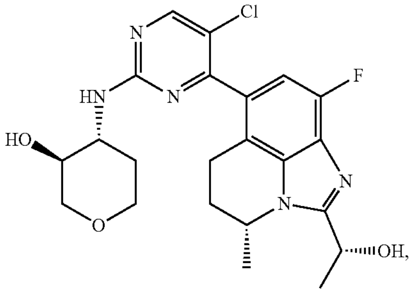
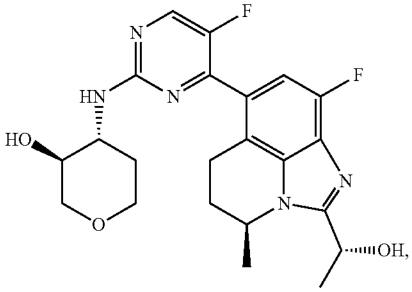
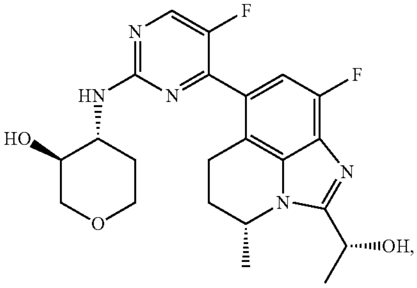
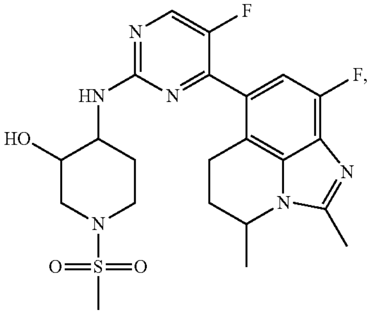

-continued
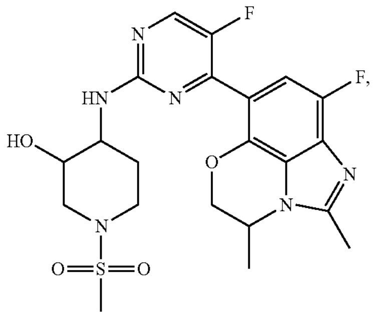
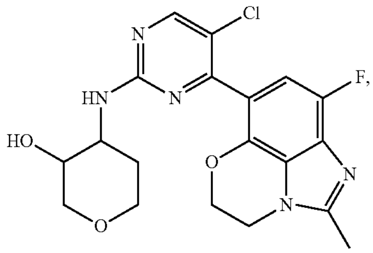
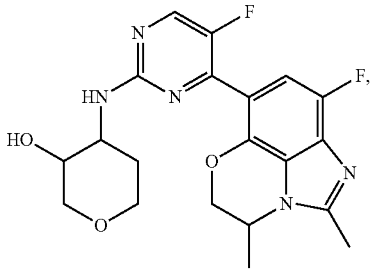
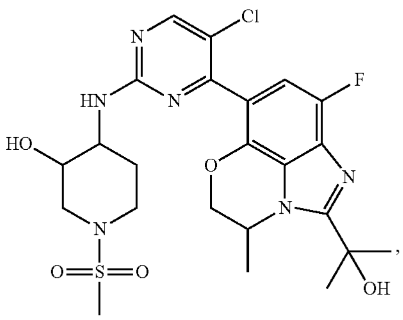
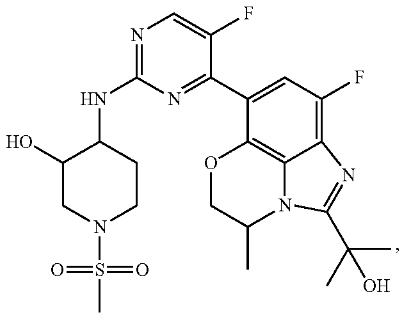
-continued
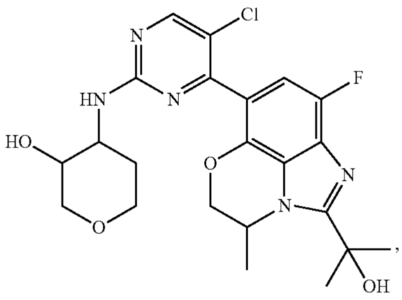
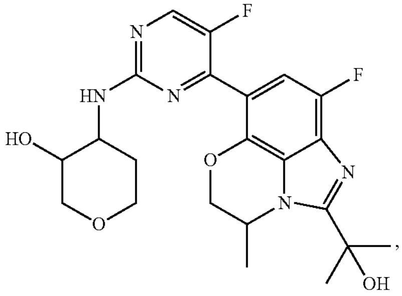
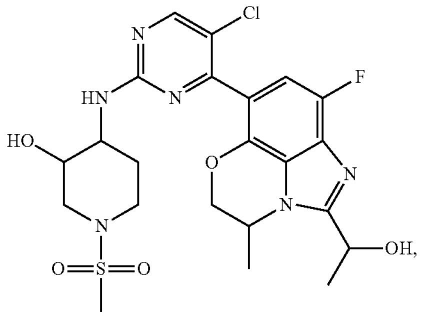
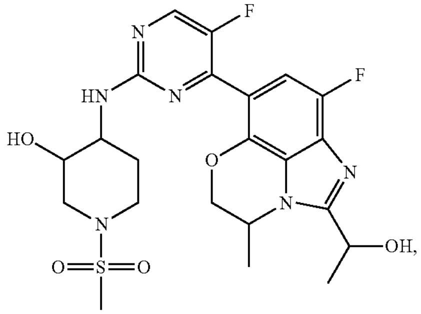
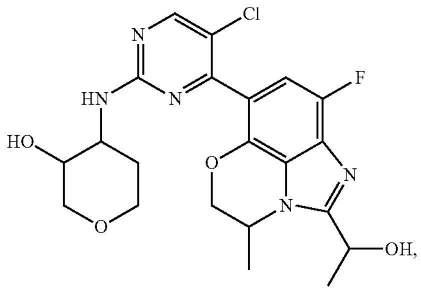

-continued
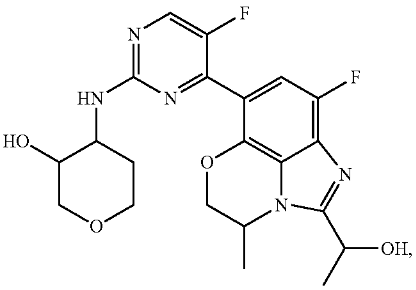
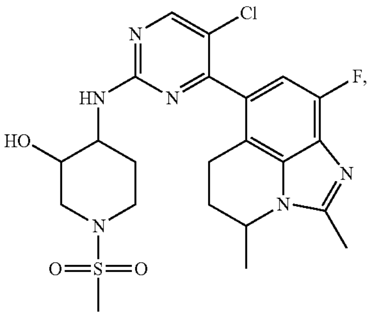
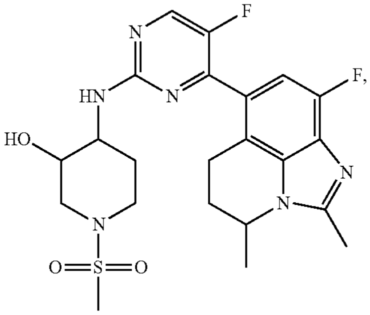
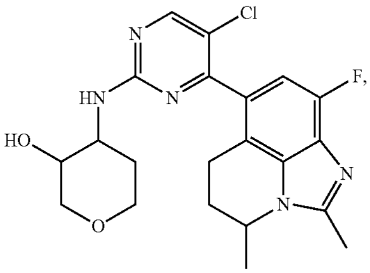
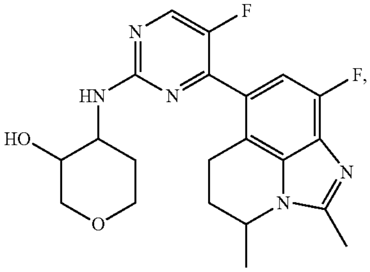
-continued
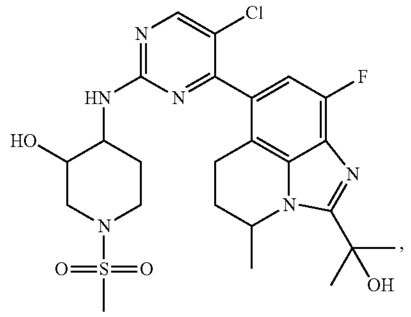
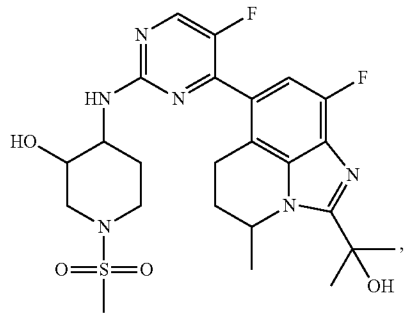
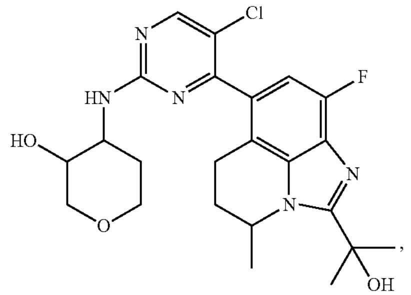
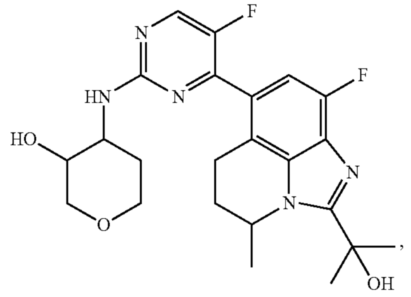
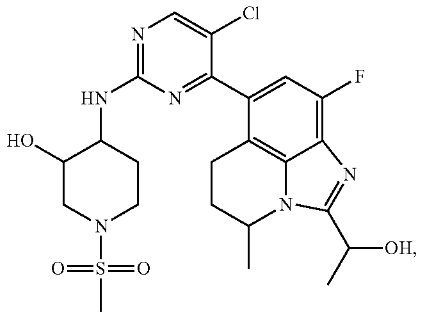

-continued

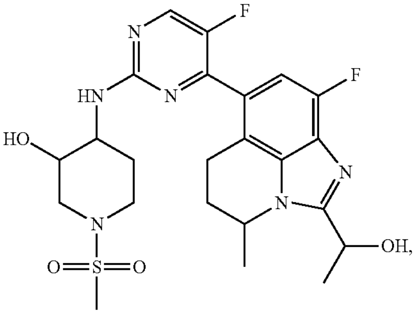

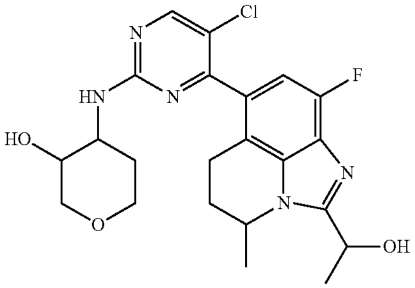

and

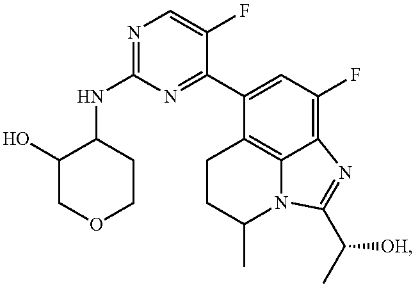

or the pharmaceutically acceptable salt thereof.

17. An isotopically substituted form of the compound of formula I or the pharmaceutically acceptable salt thereof according to claim 1, wherein the isotopically substituted form is a deuterated form.

18. A method for preparing the compound of formula I or the pharmaceutically acceptable salt thereof according to claim 1, comprising a step of reacting a compound of formula I-B with a compound of formula I-C to form the compound of formula I,

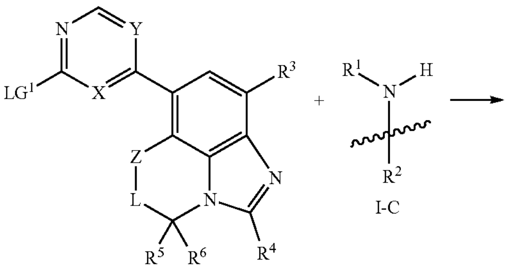

I-B

I-C

-continued

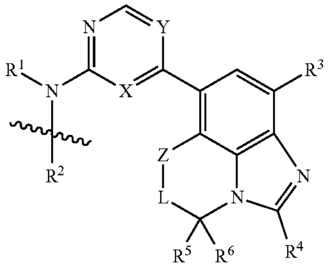

I wherein $LG^1$ is a leaving group selected from the group consisting of halogen, sulfonate, boronic acid and borate;

X, Y, Z, L, $R^1$, $R^2$, $R^3$, $R^4$, $R^5$ and $R^6$ are as defined in claim 1.

19. A pharmaceutical composition comprising the compound of formula I or the pharmaceutically acceptable salt thereof according to claim 1, and a pharmaceutically acceptable excipient.

20. A method for treating a cyclin-dependent kinase-associated disease in a patient in need thereof, the method comprising administering to the patient the compound of formula I or the pharmaceutically acceptable salt thereof according to claim 1, wherein the cyclin-dependent kinase-associated disease is cancer.

21. A method for treating cancer in a patient in need thereof, the method comprising administering to the patient the compound of formula I or the pharmaceutically acceptable salt thereof according to claim 1, wherein the cancer is selected from the group consisting of breast cancer, ovarian cancer, bladder cancer, uterine cancer, prostate cancer, lung cancer, esophageal cancer, head and neck cancer, intestinal cancer, kidney cancer, liver cancer, pancreatic cancer, gastric cancer and thyroid cancer.

22. A compound of formula I-B or a pharmaceutically acceptable salt thereof,

I-B

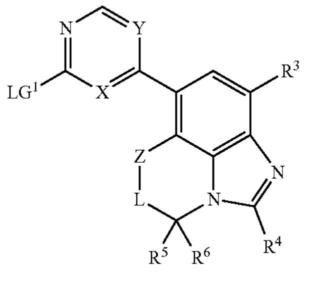

wherein $LG^1$ is a leaving group selected from the group consisting of halogen, sulfonate, boronic acid and borate; X, Y, Z, L, $R^3$, $R^4$, $R^5$ and $R^6$ are as defined in claim 1.

23. The compound of formula I or the pharmaceutically acceptable salt thereof according to claim 2, wherein $R^1$ is H.

24. The compound of formula I or the pharmaceutically acceptable salt thereof according to claim 3, wherein $R^2$ is

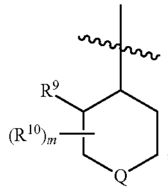, $R^9$, $R^{10}$, m and Q are as defined in claim 1.

25. The compound of formula I or the pharmaceutically acceptable salt thereof according to claim 7, wherein Y is $CR^7$; $R^7$ is selected from the group consisting of F and Cl.

26. The compound of formula I or the pharmaceutically acceptable salt thereof according to claim 8, wherein $R^3$ is selected from the group consisting of F and Cl.

27. The compound of formula I or the pharmaceutically acceptable salt thereof according to claim 9, wherein $R^4$ is $C_{1-6}$ alkyl, the $C_{1-6}$ alkyl is optionally substituted with one or more $R^b$ or deuterium atoms, and $R^b$ is OH or halogen.

28. The compound of formula I or the pharmaceutically acceptable salt thereof according to claim 10, wherein q is selected from 1; the $—(CH_2)—$ is optionally substituted with one or more substituents selected from the group consisting of H, deuterium, CN, halogen, $C_{1-6}$ alkyl, $C_{3-8}$ cycloalkyl, $C_{1-6}$ alkoxy and 3-12 membered heterocycloalkyl.

29. The compound of formula I or the pharmaceutically acceptable salt thereof according to claim 10, wherein q is selected from 1; the $—(CH_2)—$ is optionally substituted with one or more deuterium atoms.

30. The compound of formula I or the pharmaceutically acceptable salt thereof according to claim 15, wherein $R^9$ is OH;

m is 0;

$R^7$ is F or Cl;

$R^3$ is F or Cl;

$R^4$ is H or $C_{1-6}$ alkyl, the $C_{1-6}$ alkyl is optionally substituted with one or more $R^b$ or deuterium atoms; $R^b$ is selected from the group consisting of OH, CN and halogen;

$R^5$ and $R^6$ are each independently H or $C_{1-6}$ alkyl.

31. The compound of formula I or the pharmaceutically acceptable salt thereof according to claim 15, wherein $R^9$ is OH;

m is 0;

$R^7$ is F or Cl;

$R^3$ is F or Cl;

$R^4$ is H or $C_{1-6}$ alkyl, the $C_{1-6}$ alkyl is optionally substituted with one or more $R^b$ or deuterium atoms; $R^b$ is OH;

$R^5$ and $R^6$ are each independently selected from the group consisting of H, methyl, ethyl, n-propyl, isopropyl, n-butyl, isobutyl and tert-butyl.

32. The compound of formula I or the pharmaceutically acceptable salt thereof according to claim 15, wherein $R^9$ is OH;

m is 0;

$R^7$ is F or Cl;

$R^3$ is F or Cl;

$R^4$ is selected from the group consisting of H, methyl, ethyl, n-propyl, isopropyl, n-butyl, isobutyl and tert-butyl; the methyl, ethyl, n-propyl, isopropyl, n-butyl, isobutyl and tert-butyl are each independently and optionally substituted with one or more $R^b$; $R^b$ is OH;

$R^5$ and $R^6$ are each independently selected from the group consisting of H, methyl, ethyl, n-propyl, isopropyl, n-butyl, isobutyl and tert-butyl.

33. The compound of formula I or the pharmaceutically acceptable salt thereof according to claim 15, wherein $R^9$ is OH;

m is 0;

$R^7$ is F or Cl;

$R^3$ is F or Cl;

$R^4$ is selected from the group consisting of H, methyl, ethyl, n-propyl and isopropyl;

$R^5$ and $R^6$ are each independently selected from the group consisting of H, methyl, ethyl, n-propyl and isopropyl.

34. The compound of formula I or the pharmaceutically acceptable salt thereof according to claim 1, being selected from the group consisting of

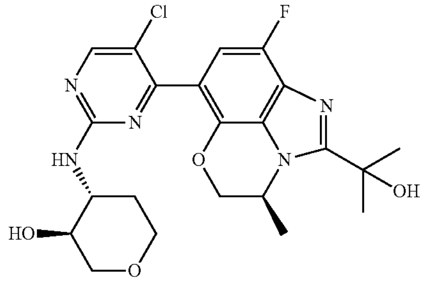

or

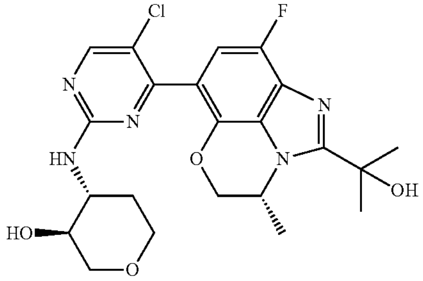

or the pharmaceutically acceptable salt thereof.

* * * * *